US011112402B2

(12) United States Patent
Movalia et al.

(10) Patent No.: US 11,112,402 B2
(45) Date of Patent: *Sep. 7, 2021

(54) REAGENTS AND METHODS FOR DETECTING PNH TYPE II WHITE BLOOD CELLS AND THEIR IDENTIFICATION AS RISK FACTORS FOR THROMBOTIC DISORDERS

(71) Applicant: Alexion Pharmaceuticals, Inc., Boston, MA (US)

(72) Inventors: Mayur Movalia, Brewer, ME (US); Andrea Illingworth, Holden, ME (US); Susan Faas McKnight, Old Lyme, CT (US); Russell P. Rother, Oklahoma City, OK (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/155,528

(22) Filed: Oct. 9, 2018

(65) Prior Publication Data

US 2019/0025293 A1 Jan. 24, 2019

Related U.S. Application Data

(62) Division of application No. 15/591,531, filed on May 10, 2017, now Pat. No. 10,126,293, which is a division of application No. 14/219,218, filed on Mar. 19, 2014, now abandoned, which is a division of application No. 13/508,909, filed as application No. PCT/US2010/055997 on Nov. 9, 2010, now abandoned.

(60) Provisional application No. 61/280,897, filed on Nov. 9, 2009.

(51) Int. Cl.
| | |
|---|---|
| *A61P 7/02* | (2006.01) |
| *G01N 33/50* | (2006.01) |
| *G01N 33/569* | (2006.01) |
| *G01N 33/68* | (2006.01) |
| *A61K 31/352* | (2006.01) |
| *A61K 31/56* | (2006.01) |
| *A61K 31/727* | (2006.01) |
| *A61K 35/19* | (2015.01) |
| *A61K 38/19* | (2006.01) |
| *A61K 38/48* | (2006.01) |
| *C07K 16/40* | (2006.01) |

(52) U.S. Cl.
CPC ....... *G01N 33/5094* (2013.01); *A61K 31/352* (2013.01); *A61K 31/56* (2013.01); *A61K 31/727* (2013.01); *A61K 35/19* (2013.01); *A61K 38/196* (2013.01); *A61K 38/4886* (2013.01); *C07K 16/40* (2013.01); *G01N 33/56972* (2013.01); *G01N 33/6893* (2013.01); *G01N 2800/226* (2013.01)

(58) Field of Classification Search
CPC .... A61K 35/19; A61K 38/196; A61K 31/352; A61K 31/56; A61K 31/727; A61K 38/4886; G01N 2800/226; G01N 33/5094; G01N 33/56972; G01N 33/6893; C07K 16/40; A61P 7/02; A61P 7/00
See application file for complete search history.

(56) References Cited

U.S. PATENT DOCUMENTS

| | | | |
|---|---|---|---|
| 5,106,741 | A | 4/1992 | Marotti et al. |
| 6,593,095 | B1 | 7/2003 | Buckley et al. |
| 10,126,293 | B2 | 11/2018 | Movalia et al. |
| 2006/0189584 | A1* | 8/2006 | Dixon ........... A61P 9/10 514/165 |
| 2007/0116710 | A1 | 5/2007 | Bell et al. |
| 2013/0045192 | A1 | 2/2013 | Movalia et al. |
| 2014/0286962 | A1 | 9/2014 | Movalia et al. |
| 2017/0285013 | A1 | 10/2017 | Movalia et al. |

FOREIGN PATENT DOCUMENTS

| | | |
|---|---|---|
| CN | 2648437 | 10/2004 |
| CN | 1636017 | 7/2005 |

OTHER PUBLICATIONS

Hillmen et al. The Complement Inhibitor Eculizumab in Paroxysmal Nocturnal Hemoglobinuria. N Engl J Med. 2006;355:1233-43.*
Ebell MH. Evidence-based initiation of warfarin (coumadin). Am Fam Physician. 2005;71(4):763-765.*
Brodsky R., "New insights into paroxysmal nocturnal hemoglobinuria," Hematology Am Soc Hematol Educ Program, vol. 516: 24-28. (2006).
Brodsky, Robert A. et al., "Improved Detection and Characterization of Paroxysmal Nocturnal Hemoglobinuria Using Fluorescent Aerolysin," Am. J. Clin. Pathol., vol. 114(3):459-466 (2000).
Dworacki, Grzegorz et al., "Flow cytometric analysis of CD55 and CD59 expression on blood cells in paroxysmal nocturnal haemoglobinuria," Folia Histochemica et Cytobiologica, vol. 43(2):117-120 (2005).
Hall, Claire et al., "Primary prophylaxis with warfarin prevents thrombosis in paroxysmal nocturnal hemoglobinuria (PNH)," Blood, vol. 102(10):3587-3591 (2003).
Hall, Sharon E. et al., "The Use of Monoclonal Antibodies and Flow Cytometry in the Diagnosis of Paroxysmal Nocturnal Hemoglobinuria," Blood, vol. 87(12):5332-5340 (1996).

(Continued)

*Primary Examiner* — Lynn Y Fan

(74) *Attorney, Agent, or Firm* — Nelson Mullins Riley & Scarborough LLP; Jane E. Remillard, Esq.; Jill Gorny Sloper, Esq.

(57) ABSTRACT

The disclosure relates to methods for detecting PNH Type II cell populations in biological samples as well as methods for determining whether a patient is at an increased risk for developing thrombocytopenia or thrombosis based on the percentage of PNH Type II cells in the patient's blood. The disclosure also features reagents and conjugates for use in the methods.

19 Claims, 2 Drawing Sheets

Specification includes a Sequence Listing.

(56) References Cited

OTHER PUBLICATIONS

Hill, Anita et al., "The Incidence and Prevalence of Paroxysmal Nocturnal Hemoglobinuria (PNH) and Survival Patients in Yorkshire," Blood, ASH Annual Meeting Abstracts, vol. 108, Abstract 985 (2006).

McMullin et al., "Tissue plasminogen activator for hepatic vein thrombosis in paroxysmal nocturnal haemoglobinuria," Journal of Internal Medicine, vol. 235:85-89 (1994).

Movalia, Mayur K., "Identification and Clinical Significance of Type II Granulocytes Among Patients with Paroxysmal Nocturnal Hemoglobinuria (PNH) Identified Using Multiparameter High-Sensitivity Flow Cytometry," Blood, 51st ASH Annual Meeting and Exposition, Abstract 3015 (2009).

Moyo, Victor M. et al., "Natural history of paroxysmal nocturnal haemoglobinuria using modern diagnostic assays," British Journal of Haematology, vol. 126:133-138 (2004).

Parker, C., et al, "Diagnosis and management of paroxysmal hemoglobinuria," Blood, vol. 106 (12): 3699-3708 (2005).

Richards, Stephen J. et al., "Application of Flow Cytometry to the Diagnosis of Paroxysmal Nocturnal Hemoglobinuria," Cytometry (Communications in Clinical Cytometry), vol. 42:223-233 (2000).

Risitano, Antonia M. et al., "Paroxysmal nocturnal hemoglobinuria: pathophysiology natural history and treatment options in the era of biological agents," Biologics: Targets & Therapy, vol. 2(2):205-222 (2008).

Rossjohn, J. et al., "Movement of a loop in domain 3 of aerolysin is required for channel formation," Biochemistry, vol. 37(2):741-746 (1998).

Sun, Ming-yan et al., "Combinative Application of Flow Cytometry and Classical Lab of Hb in Treatment of PNH," Hei Long Jiang Medical Journal, vol. 31(3):170-171 (2007).

Sutherland, D. Robert et al., "Diagnosing PNH with FLAER and Multiparameter Flow Cytometry," Cytometry Part B (Clinical Cytometry), vol. 72(3):167-177 (2007).

\* cited by examiner

SEQUENCE LISTING

```
<160> NUMBER OF SEQ ID NOS: 7

<210> SEQ ID NO 1
<211> LENGTH: 492
<212> TYPE: PRT
<213> ORGANISM: Aeromonas hydrophila

<400> SEQUENCE: 1

Gln Lys Ile Lys Leu Thr Gly Leu Ser Leu Ile Ile Ser Gly Leu Leu
1               5                   10                  15

Met Ala Gln Ala Gln Ala Ala Glu Pro Val Tyr Pro Asp Gln Leu Arg
                20                  25                  30

Leu Phe Ser Leu Gly Gln Gly Val Cys Gly Asp Lys Tyr Arg Pro Val
            35                  40                  45

Asn Arg Glu Glu Ala Gln Ser Val Lys Ser Asn Ile Val Gly Met Met
        50                  55                  60

Gly Gln Trp Gln Ile Ser Gly Leu Ala Asn Gly Trp Val Ile Met Gly
65                  70                  75                  80

Pro Gly Tyr Asn Gly Glu Ile Lys Pro Gly Thr Ala Ser Asn Thr Trp
                85                  90                  95

Cys Tyr Pro Thr Asn Pro Val Thr Gly Glu Ile Pro Thr Leu Ser Ala
                100                 105                 110

Leu Asp Ile Pro Asp Gly Asp Glu Val Asp Val Gln Trp Arg Leu Val
            115                 120                 125

His Asp Ser Ala Asn Phe Ile Lys Pro Thr Ser Tyr Leu Ala His Tyr
        130                 135                 140

Leu Gly Tyr Ala Trp Val Gly Gly Asn His Ser Gln Tyr Val Gly Glu
145                 150                 155                 160

Asp Met Asp Val Thr Arg Asp Gly Asp Gly Trp Val Ile Arg Gly Asn
                165                 170                 175

Asn Asp Gly Gly Cys Asp Gly Tyr Arg Cys Gly Asp Lys Thr Ala Ile
                180                 185                 190
```

```
Lys Val Ser Asn Phe Ala Tyr Asn Leu Asp Pro Asp Ser Phe Lys His
            195                 200                 205

Gly Asp Val Thr Gln Ser Asp Arg Gln Leu Val Lys Thr Val Val Gly
210                 215                 220

Trp Ala Val Asn Asp Ser Asp Thr Pro Gln Ser Gly Tyr Asp Val Thr
225                 230                 235                 240

Leu Arg Tyr Asp Thr Ala Thr Asn Trp Ser Lys Thr Asn Thr Tyr Gly
                245                 250                 255

Leu Ser Glu Lys Val Thr Thr Lys Asn Lys Phe Lys Trp Pro Leu Val
            260                 265                 270

Gly Glu Thr Glu Leu Ser Ile Glu Ile Ala Ala Asn Gln Ser Trp Ala
        275                 280                 285

Ser Gln Asn Gly Gly Ser Thr Thr Ser Leu Ser Gln Ser Val Arg
    290                 295                 300

Pro Thr Val Pro Ala Arg Ser Lys Ile Pro Val Lys Ile Glu Leu Tyr
305                 310                 315                 320

Lys Ala Asp Ile Ser Tyr Pro Tyr Glu Phe Lys Ala Asp Val Ser Tyr
                325                 330                 335

Asp Leu Thr Leu Ser Gly Phe Leu Arg Trp Gly Gly Asn Ala Trp Tyr
            340                 345                 350

Thr His Pro Asp Asn Arg Pro Asn Trp Asn His Thr Phe Val Ile Gly
        355                 360                 365

Pro Tyr Lys Asp Lys Ala Ser Ser Ile Arg Tyr Gln Trp Asp Lys Arg
    370                 375                 380

Tyr Ile Pro Gly Glu Val Lys Trp Trp Asp Trp Asn Trp Thr Ile Gln
385                 390                 395                 400

Gln Asn Gly Leu Ser Thr Met Gln Asn Asn Leu Ala Arg Val Leu Arg
                405                 410                 415

Pro Val Arg Ala Gly Ile Thr Gly Asp Phe Ser Ala Glu Ser Gln Phe
            420                 425                 430

Ala Gly Asn Ile Glu Ile Gly Ala Pro Val Pro Leu Ala Ala Asp Ser
        435                 440                 445

His Ser Ser Lys Leu Gln Ser Val Asp Gly Ala Gly Gln Gly Leu Arg
    450                 455                 460

Leu Glu Ile Pro Leu Asp Ala Gln Glu Leu Ser Gly Leu Gly Phe Asn
465                 470                 475                 480

Asn Val Ser Leu Ser Val Thr Pro Ala Ala Asn Gln
                485                 490

<210> SEQ ID NO 2
<211> LENGTH: 470
<212> TYPE: PRT
<213> ORGANISM: Aeromonas hydrophila

<400> SEQUENCE: 2

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60
```

```
Ile Lys Pro Gly Thr Ala Ser Asn Thr Trp Cys Tyr Pro Thr Asn Pro
 65                  70                  75                  80

Val Thr Gly Glu Ile Pro Thr Leu Ser Ala Leu Asp Ile Pro Asp Gly
                 85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Glu Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Ser Thr
370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser His Ser Ser Lys Leu Gln
            420                 425                 430

Ser Val Asp Gly Ala Gly Gln Gly Leu Arg Leu Glu Ile Pro Leu Asp
        435                 440                 445

Ala Gln Glu Leu Ser Gly Leu Gly Phe Asn Asn Val Ser Leu Ser Val
    450                 455                 460

Thr Pro Ala Ala Asn Gln
465                 470
```

-continued

```
<210> SEQ ID NO 3
<211> LENGTH: 439
<212> TYPE: PRT
<213> ORGANISM: Aeromonas hydrophila

<400> SEQUENCE: 3

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Glu Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365
```

```
Lys Trp Trp Asp Trp Asn Trp Thr Ile Gln Gln Asn Gly Leu Ser Thr
    370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser His Ser Ser Lys Leu Gln
            420                 425                 430

Ser Val Asp Gly Ala Gly Gln
            435
```

<210> SEQ ID NO 4
<211> LENGTH: 128
<212> TYPE: PRT
<213> ORGANISM: Aeromonas hydrophila

<400> SEQUENCE: 4

```
Leu Asp Pro Asp Ser Phe Lys His Gly Asp Val Thr Gln Ser Asp Arg
1               5                   10                  15

Gln Leu Val Lys Thr Val Val Gly Trp Ala Val Asn Asp Ser Asp Thr
            20                  25                  30

Pro Gln Ser Gly Tyr Asp Val Thr Leu Arg Tyr Asp Thr Ala Thr Asn
        35                  40                  45

Trp Ser Lys Thr Asn Thr Tyr Gly Leu Ser Glu Lys Val Thr Thr Lys
    50                  55                  60

Asn Lys Phe Lys Trp Pro Leu Val Gly Glu Thr Glu Leu Ser Ile Glu
65                  70                  75                  80

Ile Ala Ala Asn Gln Ser Trp Ala Ser Gln Asn Gly Gly Ser Thr Thr
                85                  90                  95

Thr Ser Leu Ser Gln Ser Val Arg Pro Thr Val Pro Ala Arg Ser Lys
            100                 105                 110

Ile Pro Val Lys Ile Glu Leu Tyr Lys Ala Asp Ile Ser Tyr Pro Tyr
            115                 120                 125
```

<210> SEQ ID NO 5
<211> LENGTH: 128
<212> TYPE: PRT
<213> ORGANISM: Aeromonas hydrophila

<400> SEQUENCE: 5

```
Leu Asp Pro Asp Ser Phe Lys His Gly Asp Val Thr Gln Ser Asp Arg
1               5                   10                  15

Gln Leu Val Lys Thr Val Val Gly Trp Ala Val Asn Asp Ser Asp Thr
            20                  25                  30

Pro Gln Ser Gly Tyr Asp Val Thr Leu Arg Tyr Asp Thr Ala Thr Asn
        35                  40                  45

Trp Ser Lys Thr Asn Thr Tyr Gly Leu Ser Glu Lys Val Thr Thr Lys
    50                  55                  60

Asn Lys Phe Lys Trp Pro Leu Val Gly Glu Cys Glu Leu Ser Ile Glu
65                  70                  75                  80

Ile Ala Ala Asn Gln Ser Trp Ala Ser Gln Asn Gly Gly Ser Thr Thr
                85                  90                  95

Thr Ser Leu Ser Gln Ser Val Arg Pro Thr Val Pro Ala Arg Ser Lys
            100                 105                 110

Ile Pro Val Lys Ile Glu Leu Tyr Lys Cys Asp Ile Ser Tyr Pro Tyr
            115                 120                 125
```

<210> SEQ ID NO 6
<211> LENGTH: 492
<212> TYPE: PRT
<213> ORGANISM: Aeromonas salmonicida

<400> SEQUENCE: 6

Met Lys Lys Leu Lys Ile Thr Gly Leu Ser Leu Ile Ile Ser Gly Leu
1               5                   10                  15

Leu Met Ala Gln Ala Gln Ala Ala Glu Pro Val Tyr Pro Asp Gln Leu
            20                  25                  30

Arg Leu Phe Ser Leu Gly Gln Glu Val Cys Gly Asp Lys Tyr Arg Pro
        35                  40                  45

Val Asn Arg Glu Glu Ala Gln Ser Val Lys Ser Asn Ile Val Gly Met
50                  55                  60

Met Gly Gln Trp Gln Ile Ser Gly Leu Ala Asn Gly Trp Val Ile Met
65                  70                  75                  80

Gly Pro Gly Tyr Asn Gly Glu Ile Lys Pro Gly Ser Ala Ser Ser Thr
                85                  90                  95

Trp Cys Tyr Pro Thr Asn Pro Ala Thr Gly Glu Ile Pro Thr Leu Ser
            100                 105                 110

Ala Leu Asp Ile Pro Asp Gly Asp Glu Val Asp Val Gln Trp Arg Leu
        115                 120                 125

Val His Asp Ser Ala Asn Phe Ile Lys Pro Thr Ser Tyr Leu Ala His
130                 135                 140

Tyr Leu Gly Tyr Ala Trp Val Gly Gly Asn His Ser Gln Tyr Val Gly
145                 150                 155                 160

Glu Asp Met Asp Val Thr Arg Asp Gly Asp Gly Trp Val Ile Arg Gly
                165                 170                 175

Asn Asn Asp Gly Gly Cys Asp Gly Tyr Arg Cys Gly Asp Lys Thr Ser
            180                 185                 190

Ile Lys Val Ser Asn Phe Ala Tyr Asn Leu Asp Pro Asp Ser Phe Lys
        195                 200                 205

His Gly Asp Val Thr Gln Ser Asp Arg Gln Leu Val Lys Thr Val Val
210                 215                 220

Gly Trp Ala Ile Asn Asp Ser Asp Thr Pro Gln Ser Gly Tyr Asp Val
225                 230                 235                 240

Thr Leu Arg Tyr Asp Thr Ala Thr Asn Trp Ser Lys Thr Asn Thr Tyr
                245                 250                 255

Gly Leu Ser Glu Lys Val Thr Thr Lys Asn Lys Phe Lys Trp Pro Leu
            260                 265                 270

Val Gly Glu Thr Glu Leu Ser Ile Glu Ile Ala Ala Asn Gln Ser Trp
        275                 280                 285

Ala Ser Gln Asn Gly Gly Ser Thr Thr Thr Ser Leu Ser Gln Ser Val
290                 295                 300

Arg Pro Thr Val Pro Ala His Ser Lys Ile Pro Val Lys Ile Glu Leu
305                 310                 315                 320

Tyr Lys Ala Asp Ile Ser Tyr Pro Tyr Glu Phe Lys Ala Asp Val Ser
                325                 330                 335

Tyr Asp Leu Thr Leu Ser Gly Phe Leu Arg Trp Gly Asn Ala Trp
            340                 345                 350

Tyr Thr His Pro Asp Asn Arg Pro Asn Trp Asn His Thr Phe Val Ile
        355                 360                 365

Gly Pro Tyr Lys Asp Lys Ala Ser Ser Ile Arg Tyr Gln Trp Asp Lys
370                 375                 380

-continued

```
Arg Tyr Ile Pro Gly Glu Val Lys Trp Ser Asp Trp Asn Trp Thr Ile
385                 390                 395                 400

Gln Gln Asn Gly Leu Ser Thr Met Gln Asn Asn Leu Ala Arg Val Leu
            405                 410                 415

Arg Pro Val Arg Ala Gly Ile Thr Gly Asp Phe Ser Ala Glu Ser Gln
        420                 425                 430

Phe Ala Gly Asn Ile Glu Ile Gly Ala Pro Val Pro Val Ala Ala Ala
        435                 440                 445

Ser Gln Ser Ser Arg Ala Arg Asn Leu Ser Ala Gly Gln Gly Leu Arg
    450                 455                 460

Leu Glu Ile Pro Leu Asp Ala Gln Glu Leu Ser Gly Leu Gly Phe Asn
465                 470                 475                 480

Asn Val Ser Leu Ser Val Thr Pro Ala Ala Asn Gln
            485                 490

<210> SEQ ID NO 7
<211> LENGTH: 469
<212> TYPE: PRT
<213> ORGANISM: Aeromonas salmonicida

<400> SEQUENCE: 7

Ala Glu Pro Val Tyr Pro Asp Gln Leu Arg Leu Phe Ser Leu Gly Gln
1               5                   10                  15

Glu Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Ser Ala Ser Ser Thr Trp Cys Tyr Pro Thr Asn Pro
65                  70                  75                  80

Ala Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ser Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Gly Trp Ala Ile Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Glu Leu Ser
                245                 250                 255

Ile Glu Ile Ala Ala Asn Gln Ser Trp Ala Ser Gln Asn Gly Gly Ser
            260                 265                 270
```

-continued

```
Thr Thr Thr Ser Leu Ser Gln Ser Val Arg Pro Thr Val Pro Ala His
        275             280             285

Ser Lys Ile Pro Val Lys Ile Glu Leu Tyr Lys Ala Asp Ile Ser Tyr
    290             295             300

Pro Tyr Glu Phe Lys Ala Asp Val Ser Tyr Asp Leu Thr Leu Ser Gly
305             310             315             320

Phe Leu Arg Trp Gly Gly Asn Ala Trp Tyr Thr His Pro Asp Asn Arg
            325             330             335

Pro Asn Trp Asn His Thr Phe Val Ile Gly Pro Tyr Lys Asp Lys Ala
            340             345             350

Ser Ser Ile Arg Tyr Gln Trp Asp Lys Arg Tyr Ile Pro Gly Glu Val
        355             360             365

Lys Trp Ser Asp Trp Asn Trp Thr Ile Gln Gln Asn Gly Leu Ser Thr
    370             375             380

Met Gln Asn Asn Leu Ala Arg Val Leu Arg Pro Val Arg Ala Gly Ile
385             390             395             400

Thr Gly Asp Phe Ser Ala Glu Ser Gln Phe Ala Gly Asn Ile Glu Ile
            405             410             415

Gly Ala Pro Val Pro Val Ala Ala Ser Gln Ser Ser Arg Ala Arg
            420             425             430

Asn Leu Ser Ala Gly Gln Gly Leu Arg Leu Glu Ile Pro Leu Asp Ala
        435             440             445

Gln Glu Leu Ser Gly Leu Gly Phe Asn Asn Val Ser Leu Ser Val Thr
    450             455             460

Pro Ala Ala Asn Gln
465
```

REAGENTS AND METHODS FOR DETECTING PNH TYPE II WHITE BLOOD CELLS AND THEIR IDENTIFICATION AS RISK FACTORS FOR THROMBOTIC DISORDERS

CROSS-REFERENCE TO RELATED APPLICATIONS

This application is a divisional of U.S. patent application Ser. No. 15/591,531, filed May 10, 2017, which is a divisional of U.S. patent application Ser. No. 14/219,218, filed Mar. 19, 2014, which is a divisional of U.S. patent application Ser. No. 13/508,909, filed Oct. 1, 2012, which is a national stage filing under 35 U.S.C. § 371 of International Application No. PCT/US2010/055997, filed on Nov. 9, 2010, which claims the benefit of the filing date under 35 U.S.C. § 119(e) to U.S. Provisional Patent Application Ser. No. 61/280,897, filed Nov. 9, 2009, the entire contents of which are incorporated herein by reference. International Application PCT/US2010/055997 was published under PCT Article 21(2) in English.

SEQUENCE LISTING

The instant application contains a Sequence Listing which has been submitted via EFS-Web and is hereby incorporated by reference in its entirety. Said ASCII copy, created on Oct. 9, 2018, is named AXJ-150USDV3_SL.txt, and is 23,333 bytes in size.

TECHNICAL FIELD

The field of the invention is medicine, immunology, molecular biology, and protein chemistry.

BACKGROUND

Paroxysmal nocturnal hemoglobinuria (PNH) is a rare, debilitating disease that is characterized by, among other things, abnormal hematopoiesis, complement-mediated intravascular hemolysis, and a propensity for thrombosis. See, e.g., Rosse and Nishimura (2003) *Int J Hematol* 77(2): 121-124 and Brodsky (2008) *Blood Rev* 22(2):65-74. PNH is caused by a somatic mutation in the X-linked phosphatidylinositol glycan complementation class A (PIGA) gene, which encodes an enzyme that is necessary for the initial step of glycosylphosphatidylinositol (GPI) anchor biosynthesis. See Miyata et al. (1993) *Science* 259:1318-1320 and Bessler et al. (1994) *EMBO J* 13:110-117. GPI anchors attach a number of proteins to the surface of hematopoietic cells. These so called GPI-anchored proteins include, among others, complement regulatory proteins such as CD55 (DAF) and CD59. Depending on the type of mutation that befalls the PIGA gene, a partial or complete loss of GPI anchor biosynthesis can result, which corresponds to a partial or complete loss in the presence of GPI-anchored proteins (e.g., GPI-anchored CD55 and CD59) on the cell surface. See Rosse (1997) *Medicine* 76:63-93. The partial or complete absence of complement regulatory proteins on the surface of red blood cells (RBCs) results in the heightened sensitivity of these cells for complement-mediated lysis and associated symptoms of PNH in afflicted patients. See Nicholson-Weller et al. (1983) *Proc Natl Acad Sci USA* 80:5066-5070 and Yamashina et al. (1990) *N Engl J Med* 323:1184-1189.

Traditionally, diagnosis of PNH and monitoring of PNH patients involved analysis of CD55 and CD59 expression on the surface of RBCs and granulocytes using flow cytometry. Sutherland et al. (2009) *Am J Clin Pathol* 132:564-572. More recently developed diagnostic methods for PNH have employed a recombinant, non-lytic form of the bacterial protein aerolysin, which binds to GPI-anchors on the surface of hematopoietic cells. See U.S. Pat. No. 6,593,095 issued to Buckley and Brodsky. Both traditional and new methods have allowed medical practitioners to classify RBCs or white blood cells from PNH patients into one of three groups: Type I cells having normal or nearly normal cell-surface expression of GPI-anchored proteins; PNH Type III cells, which have nil or completely absent cell-surface expression of GPI-anchored proteins; and PNH Type II cells having an intermediate level of cell-surface expression of GPI-anchored proteins. Brodsky et al. (2000) *Am J Clin Pathol* 114:459-466. The characterization of Type II cells among white blood cell lineages has not been performed due to the difficulty in distinguishing these cells from normal Type I white blood cells.

SUMMARY

The disclosure is based, at least in part, on the discovery by the inventors that patients having a PNH Type II white blood cell population of at least 1.2% or a PNH Type II red blood cell population of at least 0.02% are more likely to have thrombocytopenia as compared to patients who do not have PNH Type II cell populations or who have PNH Type II cell populations that are smaller than 1.2% or 0.02% for white and red blood cells, respectively. Patients with thrombocytopenia resulting from platelet destruction are much more likely to develop thrombosis, and among PNH patients, thrombosis is the leading cause of death. Accordingly, the disclosure provides methods for determining whether a patient is at an increased risk for thrombocytopenia and/or thrombosis based on the relative population of PNH Type II cells in the patient. Identification of the *nexus* between PNH Type II cells and thrombocytopenia was aided, in part, by the development of improved methods for detecting PNH Type II cells.

Thus, the disclosure also provides reagents and methods useful for detecting PNH Type II cells (e.g., Type II white blood cells and/or Type II red blood cells) in, e.g., biological samples from patients. The disclosure also provides methods for diagnosing and treating patients based on the presence or amount of PNH Type II cells in the patient. For example, the disclosure features a method for determining risk of thrombocytopenia in a patient based on the percentage of PNH Type II white blood cells detected in a biological sample from a patient suspected of having PNH. The diagnostic methods described herein have a number of advantages over prior art methods. For example, the methods described herein can more effectively separate PNH Type II white blood cells from Type I cells, which allows for a more accurate and precise measurement of the percentage of the Type II cells in a biological sample, as well as a more accurate assessment of the total PNH clone size, which comprises both Type II and Type III cells. In addition, PNH diagnostic methods that rely on GPI-expression on Type II RBCs can be unreliable because of a high turnover of red blood cells (the inherent shorter life-span of PNH Type III RBCs due to elevated sensitivity to complement-mediated lysis) and frequent RBC transfusions received by PNH patients. Therefore, the diagnostic methods described herein not only allow a practitioner to accurately and precisely quantify the percentage of Type II white blood cells in a biological sample, and thus the total abnormal clone size in the sample, but the methods are also more reliable than prior methods that relied on detecting relatively unstable populations of PNH Type II RBCs.

In one aspect, the disclosure features a method for predicting whether a patient is at an increased risk for thrombosis. The method includes determining whether a patient is at an increased risk for thrombosis based on the percentage of PNH Type II cells of the total number of cells of the same histological type (same lineage) in a biological sample from the patient indicates that the patient is at an increased risk for thrombosis.

In another aspect, the disclosure features a method for predicting whether a patient is likely to be thrombocytopenic. The method includes determining whether a patient is likely to be thrombocytopenic based on the percentage of PNH Type II cells (e.g., Type II red blood cells and/or Type II white blood cells) of the total number of cells of the same histological type (same lineage) in a biological sample from the patient indicates that the patient is likely to be thrombocytopenic.

In another aspect, the disclosure features a method for determining whether a patient is at an increased risk for thrombosis. The method includes providing (or receiving) information on the percentage of PNH Type II cells of the total cells of the same histological type (same lineage) in a biological sample from a patient; and determining whether a patient is at an increased risk for thrombosis, wherein the percentage of PNH Type II cells of the total number of cells of the same histological type in the biological sample indicates that the patient is at an increased risk for thrombosis.

In another aspect, the disclosure features a method for predicting whether a patient is at risk for developing thrombosis, which method includes determining the percentage of PNH Type II cells in a biological sample from a patient; and providing a prediction of whether the patient is at an increased risk for thrombosis, wherein the percentage of PNH Type II cells of the total number of cells of the same histological type in the biological sample indicates that the patient is at an increased risk for thrombosis.

In some embodiments, the PNH Type II cells are white blood cells (e.g., granulocytes or monocytes). In some embodiments, the PNH Type II cells are red blood cells.

In some embodiments of any of the methods described herein, the combination of a percentage of PNH type II white blood cells that is greater than or equal to 1.2% and a percentage of PNH type II red blood cells that is greater than or equal to 0.02% is predictive of whether the patient is at an increased risk of developing thrombosis or is likely to be thrombocytopenic.

In some embodiments of any of the methods described herein, the patient is at an increased risk of developing thrombosis (and/or likely to be thrombocytopenic) when the percentage of PNH Type II white blood cells is at least 1.2 (e.g., at least 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 65.3, or 70 or more) %. In some embodiments of any of the methods described herein, the patient is at an increased risk of developing thrombosis (and/or likely to be thrombocytopenic) when the percentage of PNH Type II red blood cells is at least 0.02 (e.g., at least 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 70, 71, 71.3, or 75 or more) %.

In some embodiments of any of the methods described herein, a PNH Type II white blood cell population that is between 1.2% to 65%, inclusive of 1.2% and 65%, indicates that the patient is at an increased risk for thrombosis (and/or likely to be thrombocytopenic). In some embodiments, a PNH Type II white blood cell population that is greater than or equal to 5% indicates that the patient is at an increased risk for thrombosis (and/or likely to be thrombocytopenic). In some embodiments, a PNH Type II white blood cell population that is greater than or equal to 10%, 20%, or even 50% indicates that the patient is at an increased risk for thrombosis (and/or likely to be thrombocytopenic).

In some embodiments, any of the methods described herein can further include obtaining the biological sample from the patient. The biological sample can be, e.g., a whole blood sample.

In another aspect, the disclosure features a method for predicting whether a patient is at an increased risk for developing thrombosis (and/or likely to be thrombocytopenic). The method includes determining the percentage of Type II white blood cells of the total white blood cells of the same histological type in a biological sample from a patient; and predicting whether the patient is at an increased risk for developing thrombosis, wherein the patient is at an increased risk for developing thrombosis (and/or likely to be thrombocytopenic) if the percentage of Type II white blood cells is greater than or equal to 1.2 (e.g., greater than or equal to 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 65.3, or 70 or more) %.

In another aspect, the disclosure features a method for predicting whether a patient is at an increased risk for developing thrombosis (and/or likely to be thrombocytopenic). The method includes determining the percentage of Type II red blood cells of the total red blood cells of the same histological type in a biological sample from a patient; and predicting whether the patient is at an increased risk for developing thrombosis (and/or likely to be thrombocytopenic), wherein the patient is at an increased risk for developing thrombosis (and/or likely to be thrombocytopenic) if the percentage of Type II red blood cells is greater than or equal to 0.02 (e.g., greater than or equal to 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 70, 71, 71.3, or 75 or more) %.

In yet another aspect, the disclosure features a method for selecting a therapy for a patient, which method includes selecting one or both of an anti-thrombotic therapy and an anti-thrombocytopenic therapy for a patient determined to have a PNH Type II white blood cell population of greater than or equal to 1.2 (e.g., greater than or equal to 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 65.3, or 70 or more) % and/or a PNH Type II red blood cell population of greater than or equal to 0.02 (e.g., greater than or equal to 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 70, 71, 71.3, or 75 or more) %.

In another aspect, the disclosure features a method for treating a patient. The method includes administering to a patient in need thereof one or both of an anti-thrombotic therapy and an anti-thrombocytopenic therapy if the patient is determined to have a PNH Type II white blood cell population of greater than or equal to 1.2 (e.g., greater than or equal to 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 65.3, or 70 or more) % and/or a PNH Type II red blood cell population of greater than or equal to 0.02 (e.g., greater than or equal to 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 70, 71, 71.3, or 75 or more) %.

In some embodiments of any of the methods described herein, the anti-thrombocytopenic therapy can be, e.g., platelet transfusion.

In yet another aspect, the disclosure features a computer-based method for determining whether a patient is at an increased risk for developing thrombosis, which method includes receiving data including a medical profile of a PNH patient, the profile comprising information on the percentage of PNH Type II white blood cells of the total white blood cells of the same histological type (same lineage) in a biological sample from the patient; and processing at least the portion of the data containing the information to determine whether the patient is at an increased risk for developing thrombosis, wherein the patient is at an increased risk for developing thrombosis if the percentage of Type II white blood cells is greater than or equal to 1.2 (e.g., greater than or equal to 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 65.3, or 70 or more) %.

In yet another aspect, the disclosure features a computer-based method for determining whether a patient is at an increased risk for developing thrombosis, which method includes receiving data including a medical profile of a PNH patient, the profile comprising information on the percentage of PNH Type II red blood cells of the total red blood cells of the same histological type (same lineage) in a biological sample from the patient; and processing at least the portion of the data containing the information to determine whether the patient is at an increased risk for developing thrombosis, wherein the patient is at an increased risk for developing thrombosis if the percentage of Type II red blood cells is greater than or equal to 0.02 (e.g., greater than or equal to 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 70, 71, 71.3, or 75 or more) %.

In another aspect, the disclosure features a computer-based method for determining whether a patient is at an increased risk for developing thrombosis, which method includes providing information on the percentage of PNH Type II white blood cells of the total white blood cells of the same histological type (same lineage) in a biological sample from the patient; inputting the information into a computer; and calculating a parameter indicating whether the patient is at an increased risk for thrombosis using the computer and the input information, wherein the patient is at an increased risk for developing thrombosis if the percentage of Type II white blood cells is greater than or equal to 1.2 (e.g., greater than or equal to 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 65.3, or 70 or more) %.

In another aspect, the disclosure features a computer-based method for determining whether a patient is at an increased risk for developing thrombosis, which method includes providing information on the percentage of PNH Type II white blood cells of the total white blood cells of the same histological type in a biological sample from the patient; inputting the information into a computer; and calculating a parameter indicating whether the patient is at an increased risk for thrombosis using the computer and the input information, wherein the patient is at an increased risk for developing thrombosis if the percentage of Type II white blood cells is greater than or equal to 0.02 (e.g., greater than or equal to 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 70, 71, 71.3, or 75 or more) %.

In some embodiments, any of the computer-based methods described herein can further include storing the parameter on a computer-readable medium and/or outputting the parameter.

In some embodiments, any of the methods described herein can include the step of monitoring the patient for the development of at least one symptom of thrombosis if the patient is at an increased risk of developing thrombosis. In some embodiments, any of the methods described herein can include selecting an anti-thrombotic therapy for the patient if the patient is at an increased risk of developing thrombosis. In some embodiments, any of the methods described herein can include administering to the patient an anti-thrombotic therapy if the patient is at an increased risk for developing thrombosis. The anti-thrombotic therapy can be, e.g., an anticoagulant or a thrombolytic agent. The anticoagulant can be, e.g., coumadin, heparin, or derivatives thereof. The thrombolytic agent can be, e.g., a tissue plasminogen activator, streptokinase, or a urokinase-type plasminogen activator.

In some embodiments of any of the methods described herein, a non-lytic variant form of aerolysin protein can be used to determine the percentage of PNH Type II white blood cells in the biological sample.

In some embodiments, any of the methods described herein can include recording the determined percentage of PNH Type II cells in the biological sample. In some embodiments, any of the methods described herein can include recording the prediction of whether the patient is at an increased risk for developing thrombosis or whether the patient is not at an increased risk for developing thrombosis. The recordation can be on a computer-readable medium. The recordation can also be, e.g., on a tangible medium (e.g., a patient's physical record or chart).

In yet another aspect, the disclosure features a method for classifying white blood cells. The method contacting a plurality of white blood cells with a reagent that binds to: (i) GPI or (ii) a GPI-anchored protein; and classifying one or more of the white blood cells as PNH Type II cells based on the amount of reagent bound to the cells.

In another aspect, the disclosure features a method for classifying white blood cells, which method includes contacting a plurality of white blood cells with a reagent that binds to: (i) GPI or (ii) a GPI-anchored protein; interrogating at least a portion of the white blood cells contacted with the reagent based on the amount of reagent bound to the cells; and classifying one or more of the interrogated cells as PNH Type II cells.

In another aspect, the disclosure features a method for distinguishing between different white blood cell populations. The method includes contacting a plurality of white blood cells with a reagent that binds to: (i) GPI or (ii) a GPI-anchored protein; and distinguishing at least a portion of the white blood cells from other white blood cells of the plurality based on the amount of reagent bound the cells, wherein the PNH Type II white blood cells, if present, are sufficiently distinguished from the Type I white blood cells and PNH Type III cells of the same histological type (same lineage) to allow the percentage of PNH Type II white blood cells of the total white blood cells of the same histological type in the plurality to be determined. The method can also include determining the percentage of PNH Type II white blood cells.

In yet another aspect, the disclosure features a method for determining the percentage of PNH Type II white blood cells in a sample, which method includes interrogating a plurality of white blood cells contacted with a reagent based on the amount of reagent bound to the cells, wherein the reagent binds to: (i) GPI or (ii) a GPI-anchored protein, wherein the interrogating sufficiently distinguishes the PNH Type II white blood cells, if present, from the Type I white blood cells and PNH Type III cells of the same histological type to allow the percentage of PNH Type II white blood cells of the total white blood cells of the same histological type in the plurality to be determined; and determining the percentage of PNH Type II white blood cells.

In some embodiments of any of the methods described herein, the plurality of white blood cells are contacted with a reagent that binds to GPI and a reagent that binds to a GPI-linked protein.

In some embodiments of any of the methods described herein, the distinguishing or interrogating of white blood cells (and/or the determination of the percentage of PNH Type II white blood cells) includes flow cytometry.

In some embodiments of any of the methods described herein, the plurality of white blood cells to be interrogated are obtained from a patient having, suspected of having, or at risk of developing PNH. In some embodiments, the patient is one for whom a percentage of PNH Type II red blood cells has been previously determined, but was suspect and/or inconclusive.

In some embodiments, any of the methods described herein can further include recording the percentage of PNH Type II white blood cells. The recordation can be on a computer-readable medium or a tangible medium (e.g., a patient chart or record).

In some embodiments of any of the methods described herein, the reagent can bind to a human GPI moiety. The reagent can be, e.g., an antibody or an antigen-binding fragment thereof, or an aerolysin protein. The aerolysin protein can be, e.g., a variant form of aerolysin protein that is non-lytic or is substantially non-lytic as compared to the wildtype form of the protein. The non-lytic or substantially non-lytic aerolysin protein can comprise the amino acid sequence depicted in SEQ ID NO:2 or 7 wherein the threonine at position 253 is substituted with a cysteine and the alanine at position 300 is substituted for a cysteine.

In some embodiments of any of the methods described herein, the reagent can bind to a GPI-anchored protein. For example, the reagent can be, e.g., an antibody or an antigen-binding fragment thereof that binds to a GPI-anchored protein. The GPI-anchored protein can be, e.g., alkaline phosphatase, 5' nucleotidease acetylcholinesterase, dipeptidase, LFA-3, NCAM, PH-20, CD55, CD59, Thy-1, Qa-2, CD14, CD33, CD16 (the $Fc_\gamma$ receptor III), carcinoembryonic antigen (CEA), CD24, CD66b, CD87, CD48, CD52, or any other GPI-anchored protein that is known in the art and/or set forth herein.

In some embodiments, a patient determined to have a PNH Type II white blood cell population of greater than or equal to 1.2% or a PNH Type II red blood cell population of greater than or equal to 0.02% can be diagnosed as having PNH. In some embodiments, a patient diagnosed as having PNH or a previously diagnosed PNH patient who is determined to have a PNH Type II white blood cell population greater than or equal to 1.2% or a PNH Type II red blood cell population that is greater than or equal to 0.02% can be prescribed and/or treated with a complement inhibitor such as, but not limited to, eculizumab.

In yet another aspect, the disclosure features an antibody or an antigen-binding fragment thereof that binds to a human GPI moiety. The antibody or antigen-binding fragment thereof can be, e.g., a recombinant antibody, a diabody, a chimerized or chimeric antibody, a deimmunized human antibody, a fully human antibody, a single chain antibody, an Fv fragment, an Fd fragment, an Fab fragment, an Fab' fragment, and an $F(ab')_2$ fragment.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for determining risk of thrombocytopenia or thrombosis in a subject, will be apparent from the following description, the examples, and from the claims.

DETAILED DESCRIPTION

Figure 1:
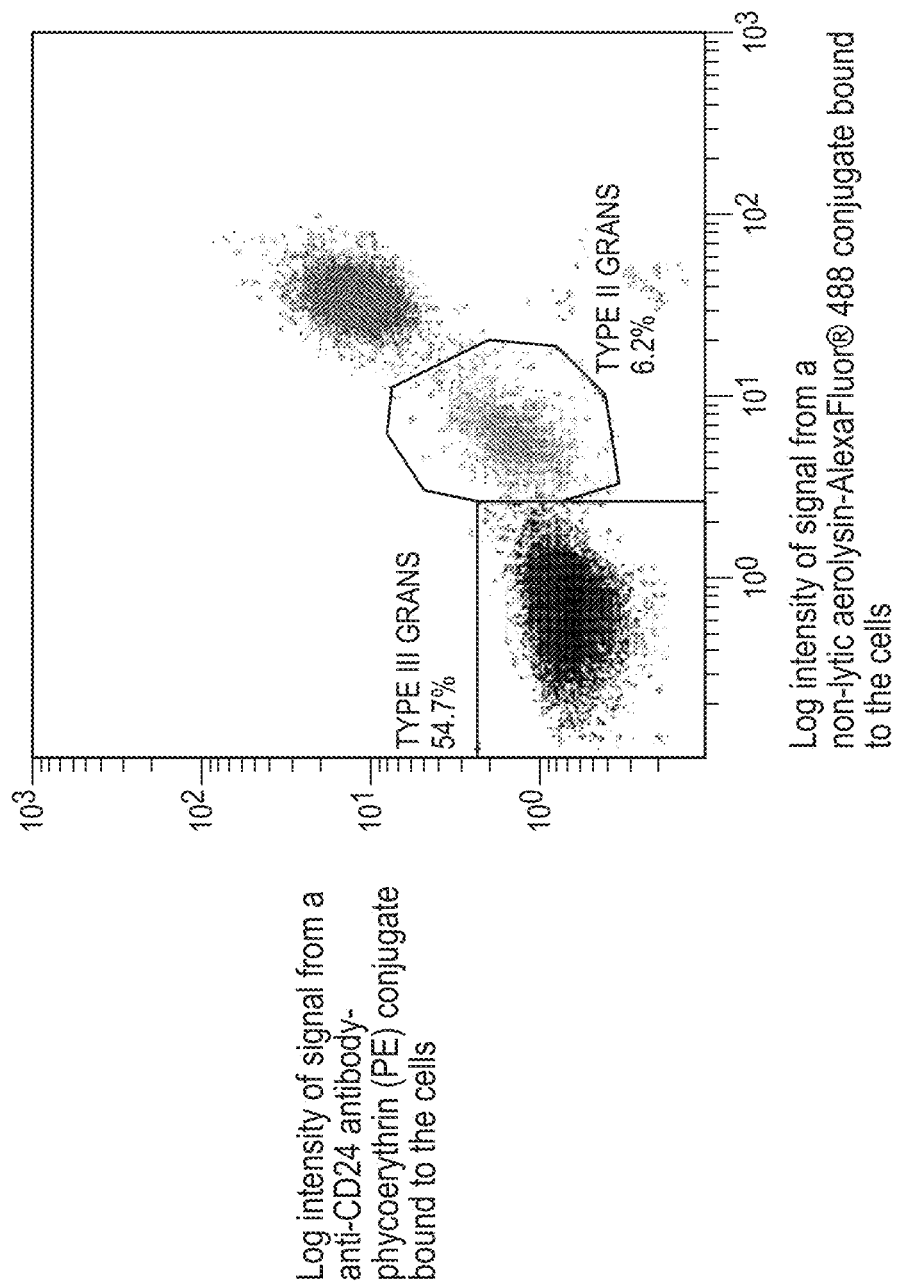
FIG. 1 is a dot plot depicting a population of human peripheral blood granulocytes that were incubated with a solution containing both a non-lytic variant of aerolysin conjugated with Alexa Fluor® 488 and an antibody that binds to CD24 conjugated to phycoerythrin (PE). The non-lytic aerolysin binds specifically to the GPI anchor, and therefore cells expressing any GPI-anchored proteins are labeled with this fluorescent protein. CD24 is a GPI-linked protein expressed on granulocytes, so cells expressing CD24 will be bound by both the anti-CD24 antibody and the non-lytic aerolysin. The X-axis represents the log intensity of detectable signal produced from the aerolysin conjugate bound to the cells and the Y-axis represents the log intensity of the detectable signal produced from the anti-CD24 antibody conjugate bound to the cells. Three populations of granulocytes are revealed by this analysis: Type III cells, which are devoid of GPI-linked proteins and thus appear unlabeled with either the anti-CD24 antibody and the non-lytic aerolysin; Type I granulocytes, which express high levels of GPI-linked proteins relative to cells lacking GPI-anchors; and Type II granulocytes, which express intermediate levels of GPI-linked proteins and thus are labeled with both the anti-CD24 and non-lytic aerolysin at lower levels than those seen on normal (Type I) granulocytes.

The present disclosure features a variety of diagnostic and therapeutic applications that are useful for, inter alia, determining whether a patient has a PNH Type II cell population and/or is at an increased risk for developing thrombocytopenia and/or thrombosis. The disclosure also features reagents that can be used in the methods. While in no way intended to be limiting, exemplary reagents, conjugates, and methods for using any of the foregoing are elaborated on below and are exemplified in the working Examples.

Reagents

The disclosure features a number of reagents that are useful in the diagnostic and therapeutic methods described herein. In some embodiments, the reagent binds to a glycosylphosphatidylinositol (GPI) moiety, which anchors many cell surface proteins to the cell membrane. GPI moieties generally contain a core of ethanolamine-HPO$_4$-6Manα1-2Manα1-6Manα1-4GlcNH$_2$1-6myo-inositol-1HPO$_4$-diacyl-glycerol (or alkylacylglycerol or ceramide). See, e.g., Paulick and Bertozzi (2008) *Biochemistry* 47(27):6991-7000. However, a number of variations on this core structure have been reported. For example, the glycan core can be modified with side chains such as, but not limited to, phosphoethanolamine, mannose, galactose, sialic acid, or other sugars. Id.

In some embodiments, the reagent can be an aerolysin protein, e.g., a non-lytic aerolysin protein. Aerolysin is a channel-forming cytolytic protein that is expressed by virulent *Aeromonas* species such as, but not limited to, *Aeromonas hydrophila* and *Aeromonas salmonicida*. Aerolysin is secreted from the bacterial cell as a 52 kDa precursor that is converted to the active form (activated) by proteolytic removal of a C-terminal peptide. The aerolysin precursor can be activated by host proteases as well as proteases secreted by an aerolysin-expressing bacterium. Once bound to a cell, aerolysin oligomerizes to produce channels in, and ultimately lyse, the cell (Howard and Buckley (1985) *J Bacteriol* 163:336-340).

The amino acid sequences of the aerolysin polypeptide produced by each of various members of the *Aeromonas* family are highly conserved. Accordingly, an aerolysin polypeptide, as used herein, can be from any species of *Aeromonas* such as, but not limited to, *A. hydrophila*, *A. caviae*, *A. veronii* (biotype *sobria*), *A veronii* (biotype *veronii*), *A. jandaei*, *A. salmonicida*, and *A. schubertii*.

In some embodiments, the aerolysin polypeptide is from *A. hydrophila* or *A. salmonicida*. In some embodiments, the aerolysin polypeptide is a proform containing a 24 amino acid signal peptide. In some embodiments, the proform aerolysin polypeptide can have, or consist of, a polypeptide having the amino acid sequence depicted in SEQ ID NO:1 or SEQ ID NO:6.

In some embodiments, the aerolysin polypeptide is a form of the protein in which the signal sequence has been removed. For example, the aerolysin polypeptide can have, or consist of, a polypeptide having an amino acid sequence depicted in SEQ ID NO:2 or SEQ ID NO:7.

In some embodiments, the aerolysin polypeptide is an active form of the protein. For example, the aerolysin polypeptide can have, or consist of, a polypeptide having an amino acid sequence depicted in SEQ ID NO:3.

As used herein, "polypeptide," "peptide," and "protein" are used interchangeably and mean any peptide-linked chain of amino acids, regardless of length or post-translational modification. The aerolysin polypeptides described herein can contain or be wildtype proteins or can be variants of the wild-type polypeptides that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The aerolysin polypeptides described herein also include "GPI-binding fragments" of the polypeptides, which are shorter than the full-length, proform polypeptides, but retain at least 10% (e.g., at least 10%, at least 15%, at least 20%, at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the active polypeptide to bind to a GPI moiety. GPI-binding fragments of an aerolysin polypeptide include terminal as well internal deletion variants of the protein. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. GPI-binding fragments can be at least 40 (e.g., at least 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, or 325 or more) amino acid residues in length (e.g., at least 40 contiguous amino acid residues of SEQ ID Nos:1-3). In some embodiments, the GPI-binding fragment of an aerolysin polypeptide is less than 400 (e.g., less than 350, 325, 300, 275, 250, 225, 200, 190, 180, 170, 160, 150, 140, 130, 120, 110, 100, 95, 90, 85, 80, 75, 60, 50, 49, 48, 47, 46, 45, 44, 43, 42, 41, or 40) amino acid residues in length (e.g., less than 400 contiguous amino acid residues of SEQ ID NOs:1-3). In some embodiments, the GPI-binding fragment of an aerolysin polypeptide is at least 40, but less than 400, amino acid residues in length.

In some embodiments, the GPI-binding fragment of an aerolysin polypeptide can include, or consist of, a polypeptide having the following amino acid sequence: L DPDSFKHGDVTQSDRQLVKTVVG-WAVNDSDTPQSGYD VTLRYDTATNWSKTN-TYGLSEKVTTKNKFKWPLVGET ELSIEIAANQS-WASQNGGSTTTSLSQSVRPTVPARSKIP VKIELYKADISYPY (SEQ ID NO:4).

In some embodiments, the GPI-binding fragment of an aerolysin polypeptide can include, or consist of, a polypeptide having the following amino acid sequence: L DPDSFKHGDVTQSDRQLVKTVVG-WAVNDSDTPQSGYD VTLRYDTATNWSKTN-TYGLSEKVTTKNKFKWPLVGEC ELSIEIAANQS-WASQNGGSTTTSLSQSVRPTVPARSKIP VKIELYKCDISYPY(SEQ ID NO:5).

In some embodiments, the aerolysin polypeptide can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100)% identical to the aerolysin sequence having the amino acid sequence depicted in any one of SEQ ID NOs:1-3, 6, or 7 (see below).

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

Depending on the intended application, in some embodiments it may be preferable to use a variant aerolysin polypeptide that lacks the ability to lyse cells. Such variant forms of the aerolysin polypeptide are known in the art and described in, e.g., Brodsky et al. (2000) *Am J Clin Pathol* 114:459-466. In some embodiments, the non-lytic, variant form of aerolysin contains, or consists of, the amino acid sequence depicted in SEQ ID NO:2 or SEQ ID NO:7 wherein one or more of: the histidine at position 132 is substituted for an asparagine (His132Asn); the glycine at position 202 is a cysteine; the threonine at position 253 is a cysteine and the alanine at position 300 is a cysteine; and the threonine at position 225 is a glycine. One exemplary non-lytic variant of aerolysin comprises the amino acid sequence depicted in SEQ ID NOs: 2 or 7, wherein the threonine at position 253 is a cysteine and the alanine at position 300 is a cysteine. As described above, the variant forms will retain the ability to bind to GPI moieties.

In some embodiments, the variant aerolysin polypeptide has less than 10 (e.g., less than 9, 8, 7, 6, 5, 4, 3, 2, or 1) % of the ability of the non-variant counterpart aerolysin polypeptide to lyse target cells. In some embodiments, the variant aerolysin polypeptide has no detectable cytolytic activity.

Methods for determining whether a variant aerolysin polypeptide binds to a GPI moiety are known in the art and exemplified in the working examples. For example, cell-based methods for detecting the binding between a variant aerolysin polypeptide and a GPI moiety on a cell surface can be determined using flow cytometry techniques and a dectectably-labeled (e.g., a fluorophore-labeled) variant aerolysin polypeptide. See, e.g., Hong et al. (2002) *EMBO J* 21(19):5047-5056.

Likewise, methods for detecting and/or quantitating the cytolytic activity of an aerolysin polypeptide or variant thereof are also known in the art. For example, the hemolytic activity of a variant Aerolysin polypeptide can be determined by contacting the variant polypeptide to normal human erythrocytes and measuring the amount of hemoglobin released from the erythrocytes. See, e.g., Howard and Buckley (1982) *Biochemistry* 21(7):1662-1667; Avigad and Bernheimer (1976) *Infection and Immunity* 13(5):1378-1381; Garland and Buckley (1988) *Infection and Immunity* 56(5):1249-1253; and Bernheimer and Avigard (1974) *Infection and Immunity* 9:1016-1021. A decreased amount, or the absence of, cytolytic activity by the variant, as compared to the amount of cytolytic activity possessed by the non-variant counterpart polypeptide, is an indication that the variant polypeptide has reduced or absent cytolytic activity.

Methods for obtaining an aerolysin polypeptide, or producing a variant of the polypeptide as described herein, are known in the art of molecular biology and exemplified in the working Examples. See, e.g., Sambrook et al. (1989) "Molecular Cloning: A Laboratory Manual, 2$^{nd}$ Edition," Cold Spring Harbor Laboratory Press, Cold Spring Harbor, N.Y. and Ausubel et al. (1992) "Current Protocols in Molecular Biology," Greene Publishing Associates. Template DNA encoding an aerolysin polypeptide can be obtained from any of the *Aeromonas* species described herein using standard techniques (see, e.g., Sambrook et al. (1989), supra). For example, Howard et al. describes the isolation and characterization of a nucleic acid sequence encoding an aerolysin polypeptide from *Aeromonas hydrophila* (Howard et al. (1987) *J Bacteriol* 169(6):2869-2871). An aerolysin polypeptide isolated from *Aeromonas salmonicida* is described in Buckley (1990) *Biochem. Cell Biol.* 68:221-224 and Wong et al. (1989) *J Bacteriol.* 171:2523-2527.

In some embodiments, an aerolysin polypeptide can contain internal or terminal (carboxy or amino-terminal) irrelevant or heterologous amino acid sequences (e.g., sequences derived from other proteins or synthetic sequences not corresponding to any naturally occurring protein). The sequences can be, for example, an antigenic tag (e.g., FLAG, polyhistidine, hemagglutinin (HA), glutathione-S-transferase (GST), or maltose-binding protein (MBP)). Heterologous sequences can also include proteins useful as diagnostic or detectable markers, for example, luciferase, green fluorescent protein (GFP), or chloramphenicol acetyl transferase (CAT).

Exemplary aerolysin polypeptides as well as methods for preparing and purifying the polypeptides are described in U.S. provisional patent application Ser. No. 61/200,655, the disclosure of which is incorporated herein by reference in its entirety.

In some embodiments, the reagent can be an antibody that binds to a GPI moiety. Antibodies that bind to non-human GPI moieties have been identified and isolated. See, e.g., Naik et al. (2006) *Infection and Immunity* 74(2):1412 (isolation of a naturally-occurring antibody that binds to the GPI moieties of *Plasmodium falciparum*.). As described in detail herein, it is well within the capability of an ordinarily skilled artisan to generate an antibody that binds to a human GPI moiety.

As used herein, the term "antibody" refers to a whole or intact antibody molecule (e.g., IgM, IgG (including IgG1, IgG2, IgG3, and IgG4), IgA, IgD, or IgE) or any antigen-binding fragment thereof. The term antibody includes, e.g., a chimerized or chimeric antibody, a humanized antibody, a deimmunized antibody, and a fully human antibody. Antigen-binding fragments of an antibody include, e.g., a single chain antibody, a single chain Fv fragment (scFv), an Fd fragment, an Fab fragment, an Fab' fragment, or an $F(ab')_2$ fragment. An scFv fragment is a single polypeptide chain that includes both the heavy and light chain variable regions of the antibody from which the scFv is derived. In addition, intrabodies, minibodies, triabodies, and diabodies (see, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283, the disclosures of each of which are incorporated herein by reference in their entirety) are also included in the definition of antibody and are compatible for use in the methods described herein. Bispecific antibodies are also embraced by the term "antibody." Bispecific antibodies are monoclonal, preferably human or humanized, antibodies that have binding specificities for at least two different antigens. Methods for generating an antibody or a fragment thereof are discussed herein.

In some embodiments, the reagent can bind to a GPI-anchored protein. For example, the reagent can be an antibody that binds to a GPI-anchored protein. In some embodiments, the reagent can be a ligand for a GPI-anchored protein. GPI-anchored proteins are myriad and include, without limitation, alkaline phosphatase, 5' nucleotidease acetylcholinesterase, dipeptidase, LFA-3, NCAM, PH-20, CD55, CD59, Thy-1, Qa-2, CD14, CD33, CD16 (the $Fc_\gamma$ receptor III), carcinoembryonic antigen (CEA), and CD52. Antibodies that bind to GPI-anchored proteins are well known in the art and are described in, e.g., Hall and Rosse (1996) supra, Richards et al. (2008) *Cytometry B Clin Cytom* 76B(1):47-55; Richards and Barnett (2007) *Clin Lab Med* 27(3):577-590; Luzzatto et al. (2006) *Int J Hematol* 84(2):104-112; and Thomason et al. (2004) *Am J Clin Pathol* 122(1):128-134. Such antibodies are also commercially available from, e.g., Santa Cruz Biotechnology, Inc. (Santa Cruz, Calif.), Novus Biologicals (Littleton, Colo.), and R&D Systems (Minneapolis, Minn.).

Suitable methods for generating an antibody that binds to a GPI-anchored protein or a GPI moiety for use in the diagnostic and/or therapeutic methods described are well known in the art and described in the following section.

Methods for Generating an Antibody

Suitable methods for producing an antibody (e.g., an antibody that binds to a GPI moiety or a GPI-anchored protein), or antigen-binding fragments thereof, in accordance with the disclosure are known in the art and described herein. For example, monoclonal anti-CD55 antibodies may be generated using human CD55-expressing cells, a CD55 polypeptide, or an antigenic fragment of CD55 polypeptide, as an immunogen, thus raising an immune response in animals from which antibody-producing cells and in turn monoclonal antibodies may be isolated. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to a GPI-anchored protein or a GPI moiety.

Moreover, antibodies derived from recombinant libraries ("phage antibodies") may be selected using, e.g., cells expressing a GPI moiety or a GPI-anchored protein, recombinant GPI-linked proteins, or free GPI moieties as bait to isolate the antibodies or polypeptides on the basis of target specificity. The production and isolation of non-human and chimeric antibodies are well within the purview of the skilled artisan.

Recombinant DNA technology can be used to modify one or more characteristics of the antibodies produced in non-human cells. Thus, chimeric antibodies can be constructed in order to decrease the immunogenicity thereof in diagnostic or therapeutic applications. Moreover, immunogenicity can be minimized by humanizing the antibodies by CDR grafting and, optionally, framework modification. See, U.S. Pat. Nos. 5,225,539 and 7,393,648, the contents of each of which are incorporated herein by reference.

Antibodies can be obtained from animal serum or, in the case of monoclonal antibodies or fragments thereof, produced in cell culture. Recombinant DNA technology can be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g. *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic (e.g., bicistronic) DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibers, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) *Nature* 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, e.g.: WO97/08320; U.S. Pat. Nos. 5,427,908; 5,508,717; Smith (1985) *Science* 225:1315-1317; Parmley and Smith (1988) *Gene* 73:305-318; De La Cruz et al. (1988) *Journal of Biological Chemistry* 263:4318-4322; U.S. Pat. Nos. 5,403,484; 5,223,409; WO88/06630; WO92/15679; U.S. Pat. Nos. 5,780,279; 5,571,698; 6,040,136; Davis et al. (1999) *Cancer Metastasis Rev.* 18(4):421-5; and Taylor et al. (1992) *Nucleic Acids Research* 20: 6287-6295; Tomizuka et al. (2000) *Proc. Natl. Acad. Sci. USA* 97(2): 722-727, the contents of each of which are incorporated herein by reference in their entirety.

The cell culture supernatants are screened for the desired antibodies, preferentially by immunofluorescent staining of GPI or GPI-anchored protein-expressing cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with a GPI-moiety, a cell expressing GPI-anchors at its surface, a GPI-anchored polypeptide, a cell expressing a GPI-anchored protein at its surface, or with Protein-A or -G.

Another embodiment provides a process for the preparation of a bacterial cell line secreting antibodies directed against a GPI moiety or a GPI-anchored protein in a suitable mammal. For example, a rabbit is immunized with a GPI-moiety, a cell expressing GPI-anchors at its surface, a GPI-anchored polypeptide, a cell expressing a GPI-anchored protein at its surface, or fragments thereof. A phage display library produced from the immunized rabbit is constructed and panned for the desired antibodies in accordance with methods well known in the art (such as, e.g., the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be expanded from deep-frozen cultures by thawing and propagation in vitro or as ascites in vivo.

In another embodiment, a process is provided for the preparation of a hybridoma cell line secreting monoclonal antibodies against a GPI moiety or a GPI-anchored protein. In that process, a suitable mammal, for example a Balb/c mouse, is immunized with one or more polypeptides or antigenic fragments of, e.g., CD55 or CD14 or with one or more polypeptides or antigenic fragments derived from a CD55-expressing cell, the CD55-expressing cell itself, or an antigenic carrier containing a purified polypeptide as described. Similarly, the mammal can be immunized with a human GPI moiety, a fragment thereof, or cells that express the human GPI moiety, perhaps at a high amount. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with, e.g., a GPI-anchored protein or a GPI moiety are fused with cells of the myeloma cell line PAI or the myeloma cell line Sp2/0-Ag 14. The obtained hybrid cells are then screened for secretion of the desired antibodies and positive hybridoma cells are cloned.

Methods for preparing a hybridoma cell line include immunizing Balb/c mice by injecting subcutaneously and/or intraperitoneally an antigen of interest several times, e.g., four to six times, over several months, e.g., between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described supra, supplemented with a selection medium, for example HAT medium, at regular intervals in order to prevent normal myeloma cells from overgrowing the desired hybridoma cells.

The antibodies and fragments thereof can be "chimeric." Chimeric antibodies and antigen-binding fragments thereof comprise portions from two or more different species (e.g., mouse and human). Chimeric antibodies can be produced with mouse variable regions of desired specificity spliced into human constant domain gene segments (for example, U.S. Pat. No. 4,816,567). In this manner, non-human antibodies can be modified to make them more suitable for human clinical application (e.g., methods for detecting Type II PNH cells).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (see, e.g., Jones et al. (1986) *Nature* 321:522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. (See, e.g., Jakobovits et al. (1993) *Proc. Natl. Acad. Sci. USA* 90:2551; Jakobovits et al. (1993) *Nature* 362:255-258; Bruggemann et al. (1993) *Year in Immunol.* 7:33; and Duchosal et al. (1992) *Nature* 355:258.) Transgenic mice strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., a GPI moiety or a GPI-anchored protein such as CD55 or CD14) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al. (1991) *J. Mol. Biol.* 227:381; Marks et al. (1991) *J. Mol. Biol.*, 222:581-597; and Vaughan et al. (1996) *Nature Biotech* 14:309 (1996)). Synthetic phage libraries can be created which use randomized combinations of synthetic human antibody V-regions. By selection on antigen fully human antibodies can be made in which the V-regions are very human-like in nature. See, e.g., U.S. Pat. Nos. 6,794,132, 6,680,209, 4,634,666, and Ostberg et al. (1983), *Hybridoma* 2:361-367, the contents of each of which are incorporated herein by reference in their entirety.

For the generation of human antibodies, also see Mendez et al. (1998) *Nature Genetics* 15:146-156, Green and Jakobovits (1998) *J. Exp. Med.* 188:483-495, the disclosures of which are hereby incorporated by reference in their entirety.

Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Publication Nos. 20030229905 A1, 20040010810 A1, US 20040093622 A1, 20060040363 A1, 20050054055 A1, 20050076395 A1, 20050287630 A1. See also International Publication Nos. WO 94/02602, WO 96/34096, and WO 98/24893, and European Patent No. EP 0 463 151 B1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more JH genes, a mu constant region, and a second constant region (preferably a gamma constant region) are formed into a construct for insertion into an animal. This approach is described in, e.g., U.S. Pat. Nos. 5,545,807; 5,545,806; 5,625,825; 5,625,126; 5,633,425; 5,661,016; 5,770,429; 5,789,650; and 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference. See also European Patent No. 0 546 073 B1, International Patent Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) *Nucleic Acids Res.* 20: 6287; Chen et al. (1993) *Int. Immunol.* 5: 647; Tuaillon et al. (1993) *Proc. Natl. Acad. Sci. USA* 90: 3720-4; Choi et al. (1993) *Nature Genetics* 4: 117; Lonberg et al. (1994) *Nature* 368: 856-859; Taylor et al. (1994) *International Immunology* 6: 579-591; Tuaillon et al. (1995) *J. Immunol.* 154: 6453-65; Fishwild et al. (1996) *Nature Biotechnology* 14: 845; and Tuaillon et al. (2000) *Eur. J. Immunol.* 10: 2998-3005, the disclosures of each of which are hereby incorporated by reference in their entirety.

In certain embodiments, de-immunized antibodies (e.g., antibodies that bind to a human GPI moiety or to a GPI-anchored protein) or antigen-binding fragments thereof are provided. De-immunized antibodies or antigen-binding fragments thereof may be modified so as to render the antibody or antigen-binding fragment thereof non-immunogenic, or less immunogenic, to a given species. De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized antibodies described herein include de-immunized antigen-binding fragments, Fab, Fv, scFv, Fab' and F(ab)$_2$, monoclonal antibodies, murine antibodies, engineered antibodies (such as, for example, chimeric, single chain, CDR-grafted, humanized, fully human antibodies, and artificially selected antibodies), synthetic antibodies and semi-synthetic antibodies.

In some embodiments, a recombinant DNA comprising an insert coding for a heavy chain variable domain and/or for a light chain variable domain of an antibody-expressing cell line is produced. The term DNA includes coding single stranded DNAs, double stranded DNAs consisting of said coding DNAs and of complementary DNAs thereto, or these complementary (single stranded) DNAs themselves.

Furthermore, a DNA encoding a heavy chain variable domain and/or a light chain variable domain of an antibody (e.g., an anti-GPI antibody or an anti-GPI-anchored protein antibody) can be enzymatically or chemically synthesized to contain the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an antibody of interest fused to a human constant domain IgG, for example γ1, γ2, γ3 or γ4, in particular embodiments γ1 or γ4, may be used. Recombinant DNAs including an insert coding for a light chain murine variable domain of an antibody fused to a human constant domain κ or λ, preferably κ, are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent. The DNA coding for an agent is intended to be a DNA coding for the agent useful in diagnostic or therapeutic applications. Thus, agent molecules which are toxins or enzymes, especially enzymes capable of catalyzing the activation of prodrugs, are particularly indicated. The DNA encoding such an agent has the sequence of a naturally occurring enzyme or toxin encoding DNA, or a mutant thereof, and can be prepared by methods well known in the art.

Accordingly, the monoclonal antibodies or antigen-binding fragments of the disclosure can be naked antibodies or antigen-binding fragments that are not conjugated to other agents, for example, a therapeutic agent or detectable label. Alternatively, the monoclonal antibody or antigen-binding fragment can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an antibody or an antigen-binding fragment thereof (e.g., Fab, Fv, single-chain scFv, Fab', and F(ab')$_2$) is linked to a molecule that increases the half-life of the antibody or antigen-binding fragment (see the section entitled "Conjugates").

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc. Natl. Acad. Sci. USA,* 78:2072) or Tn5 neo (Southern and Berg (1982) *Mol. Appl. Genet.* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc. Natl. Acad. Sci. USA,* 79:7147), polyoma virus (Deans et al. (1984) *Proc. Natl. Acad. Sci. USA* 81:1292), or SV40 virus (Lusky and Botchan (1981) *Nature* 293:79).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983)*Mol. Cell Biol.* 3:280; Cepko et al. (1984) *Cell* 37:1053; and Kaufman (1985) *Proc. Natl. Acad. Sci. USA* 82:689.

As is evident from the disclosure, the anti-GPI moiety antibodies or anti-GPI-anchored protein antibodies can be used in methods for diagnosing disease (e.g., diagnosing PNH or an increased risk of developing thrombocytopenia), monitoring of disease progression, and the selection of appropriate therapies, including combination therapies, for treating PNH, thrombocytopenia, or thrombosis in a subject.

In the diagnostic embodiments of the present disclosure, bispecific antibodies are contemplated. Bispecific antibodies are monoclonal, preferably human or humanized, antibodies that have binding specificities for at least two different antigens. In the present case, one of the binding specificities is for a GPI moiety or a GPI-anchored protein on a cell (such as, e.g., a white blood cell or a red blood cell), the other one is for any other antigen, and preferably for a cell-surface protein or receptor or receptor subunit.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello (1983) *Nature* 305:537-539). Antibody variable domains with the desired binding specificities (antibody-antigen combining sites) can be fused to immunoglobulin constant domain sequences. The fusion preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) *Methods in Enzymology* 121:210; PCT Publication No. WO 96/27011; Brennan et al. (1985) *Science* 229:81; Shalaby et al., *J. Exp. Med.* (1992) 175:217-225; Kostelny et al. (1992) *J. Immunol.* 148(5):1547-1553; Hollinger et al. (1993) *Proc. Natl. Acad. Sci. USA* 90:6444-6448; Gruber et al. (1994) *J. Immunol.* 152:5368; and Tutt et al. (1991) *J. Immunol.* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. (See, e.g., Kostelny et al. (1992) *J Immunol.* 148(5):1547-1553). The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc. Natl. Acad. Sci. USA* 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. (See, e.g., Gruber et al. (1994) *J. Immunol.* 152:5368.) Alternatively, the antibodies can be "linear antibodies" as described in, e.g., Zapata et al. (1995) *Protein Eng.* 8(10):1057-1062. Briefly, these antibodies comprise a pair of tandem Fd segments ($V_H$-$C_H1$-$V_H$-$C_H1$) which form a pair of antigen binding regions. Linear antibodies can be bispecific or monospecific.

Conjugates

In some embodiments, a reagent described herein (e.g., a non-lytic aerolysin polypeptide or an antibody that binds to a GPI moiety or a GPI-anchored protein) can be conjugated to a heterologous moiety. The heterologous moiety can be, e.g., a heterologous protein (see above), a therapeutic agent (e.g., a toxin or a drug), or a detectable label such as, but not limited to, a radioactive label, an enzymatic label, a fluorescent label, or a luminescent label. Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), Alexa Fluor® 488, Alexa Fluor® 647, GFP, DyLight 488, phycoerythrin (PE), propidium iodide (PI), PerCP, PE-Alexa Fluor® 700, Cy5, allophycocyanin, Cy7, and PE-Alexa Fluor® 750. Luminescent labels include, e.g., any of a variety of luminescent lanthanide (e.g., europium or terbium) chelates. For example, suitable europium chelates include the europium chelate of diethylene triamine pentaacetic acid (DTPA). Enzymatic labels include, e.g., alkaline phosphatase, CAT, luciferase, and horseradish peroxidase.

Suitable methods for conjugating a heterologous moiety to the reagent are well-known in the art of protein chemistry. For example, two proteins can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α (2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane) an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

Radioactive labels can be conjugated to the reagent by covalent or non-covalent (e.g., ionic or hydrophobic) bonds. They can be bound to any part of the protein provided that the conjugation does not interfere with the ability of the reagent to bind to a GPI moiety or to a GPI-anchored protein. In some embodiments, where the reagent is a protein, the radioactive label can be directly conjugated to the amino acid backbone of the reagent. Alternatively, the radioactive label can be included as part of a larger molecule (e.g., $^{125}I$ in meta-[$^{125}I$]iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) *J. Nucl. Med.* 38:1221-1229) or chelate (e.g., to DOTA or DTPA) which is in turn bound to the protein backbone. Methods of conjugating the radioactive labels or larger molecules/chelates containing them to the reagents described herein are also known in the art. Such methods involve incubating the reagent with the radioactive label under conditions (e.g., pH, salt concentration, and/or temperature) that facilitate binding of the radioactive label or chelate to the reagent (see, e.g. U.S. Pat. No. 6,001,329, the disclosure of which is incorporated herein by reference in its entirety).

Methods for conjugating a fluorescent label (sometimes referred to as a "fluorophore") to a reagent (e.g., a non-lytic aerolysin protein or an antibody) are known in the art of protein chemistry. For example, fluorophores can be conjugated to free amino groups (e.g., of lysines) or sulfhydryl groups (e.g., cysteines) of proteins using succinimidyl (NETS) ester or TFP ester moieties attached to the fluorophores. In some embodiments, the fluorophores can be conjugated to a heterobifunctional cross-linker moiety such as sulfo-SMCC. Suitable conjugation methods involve incubating the reagent with the fluorophore under conditions that facilitate binding of the fluorophore to the reagent. See, e.g., Welch and Redvanly (2003) "Handbook of Radiopharmaceuticals: Radiochemistry and Applications," John Wiley and Sons (ISBN: 0471495603). A variety of kits are commercially available for use in conjugating a fluorophore to a protein, e.g., the Alexa Fluor® 488 Protein Labeling Kit and the Alexa Fluor® 647 Protein Labeling Kit (Molecular Probes, Invitrogen™) In some embodiments, the fluorophore can be conjugated to a reagent at 1-2 mol dye per mol of protein.

In some embodiments, the reagents (e.g., an aerolysin protein or an antibody that binds to a GPI moiety or a GPI-anchored protein) can be modified, e.g., with a moiety that improves the stabilization and/or retention of the antibodies themselves in circulation, e.g., in blood, serum, or other tissues. For example, a reagent described herein can be PEGylated as described in, e.g., Lee et al. (1999) *Bioconjug. Chem* 10(6): 973-8; Kinstler et al. (2002) *Advanced Drug Deliveries Reviews* 54:477-485; and Roberts et al. (2002) *Advanced Drug Delivery Reviews* 54:459-476. The stabilization moiety can improve the stability, or retention of, the reagent in a subject's body (e.g., blood or tissue) by at least 1.5 (e.g., at least 2, 5, 10, 15, 20, 25, 30, 40, or 50 or more) fold.

Biological Samples and Sample Collection

Suitable biological samples for use in the methods described herein include any biological fluid, population of cells, or tissue or fraction thereof, which includes one or more white blood cells and/or one or more red blood cells. A biological sample can be, for example, a specimen obtained from a subject (e.g., a mammal such as a human) or can be derived from such a subject. For example, a sample can be a tissue section obtained by biopsy, or cells that are placed in or adapted to tissue culture. A biological sample can also be a biological fluid such as urine, whole blood or a fraction thereof (e.g., plasma), saliva, semen, sputum, cerebral spinal fluid, tears, or mucus. A biological sample can be further fractionated, if desired, to a fraction containing particular cell types. For example, a whole blood sample can be fractionated into serum or into fractions containing particular types of blood cells such as red blood cells or white blood cells (leukocytes). If desired, a biological sample can be a combination of different biological samples from a subject such as a combination of a tissue and fluid sample.

The biological samples can be obtained from a subject, e.g., a subject having, suspected of having, or at risk of developing, paroxysmal nocturnal hemoglobinuria (PNH). Any suitable methods for obtaining the biological samples can be employed, although exemplary methods include, e.g., phlebotomy, swab (e.g., buccal swab), lavage, or fine needle aspirate biopsy procedure. Non-limiting examples of tissues susceptible to fine needle aspiration include lymph node, lung, thyroid, breast, and liver. Biological samples can also be obtained from bone marrow. Samples can also be collected, e.g., by microdissection (e.g., laser capture microdissection (LCM) or laser microdissection (LMD)), bladder wash, smear (PAP smear), or ductal lavage.

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes in the cells (e.g., changes in osmolarity or pH) or denaturation of cell surface proteins (e.g., GPI-linked proteins) or GPI moieties on the surface of the cells. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, e.g., Pollard and Walker (1997), "Basic Cell Culture Protocols," volume 75 of *Methods in Molecular Biology*, Humana Press; Masters (2000) "Animal cell culture: a practical approach," volume 232 of *Practical approach series*, Oxford University Press; and Jones (1996) "Human cell culture protocols," volume 2 of *Methods in molecular medicine*, Humana Press".

A sample also can be processed to eliminate or minimize the presence of interfering substances. For example, a biological sample can be fractionated or purified to remove one or more materials (e.g., cells) that are not of interest. Methods of fractionating or purifying a biological sample include, but are not limited to, flow cytometry, fluorescence activated cell sorting, and sedimentation.

Diagnostic and Therapeutic Methods

As noted above and elaborated on in the working examples, the inventors have discovered a clinical relationship between the presence or amount of PNH Type II hematopoietic cells (e.g., Type II white blood cells and/or Type II red blood cells) and thrombocytopenia in a patient. For example, the inventors have determined that a patient with a PNH Type II white blood cell population of at least 1.2 (e.g., at least 1.2, 1.5, 2, 3, 5, 7, 9, 10, 12, 15, 17, 20, 22, 25, 27, 30, 32, 35, 37, 40, 42, 45, 47, 50, 52, 55, 57, 60, 62, 65, or 65.3 or more) % as compared to the total white blood cells of the same histological type (the same lineage) in the biological sample tested is much more likely to be thrombocytopenic than a patient who does not have a detectable PNH Type II white blood cell population or a patient with a PNH Type II white blood cell population lower than 1.2%. Patient samples with PNH Type II granulocyte populations had similar peripheral white blood cell counts, peripheral red blood cell counts, absolute neutrophil counts, and hemoglobin (Hgb) levels, compared to patient samples without detectable Type II granulocyte populations, indicating that differences in platelet counts are likely not due to differences in underlying bone marrow production. In other words, the decreased platelet counts in patients with detectable PNH Type II granulocyte clones may be due to increased terminal complement-mediated platelet consumption or destruction, which can be associated with thrombosis, the leading cause of death among PNH patients. See, e.g., Franchini (2006) *Hematology* 11(3):139-146. Accordingly, the present disclosure features methods for using information related to the percentage of PNH Type II white blood cells in a patient sample for determining whether the patient is at an increased risk of developing thrombocytopenia and/or thrombosis. Similarly, the inventors have determined that a patient with a PNH Type II RBC population of at least 0.02 (e.g., at least 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 70, 71, 71.3, or 75 or more) % is much more likely to be thrombocytopenic than a patient who does not have a detectable PNH Type II RBC population or a patient with a PNH Type II RBC population lower than 0.02%. Thus, the present disclosure also features methods for using information related to the PNH Type II RBC clone size in a patient for determining whether the patient is at risk of developing thrombocytopenia and/or thrombosis.

The following methods can be employed to detect the presence, or to determine the percentage, of PNH Type II hematopoietic cells (e.g., Type II PNH white blood cells) as compared to the total amount of cells of the same histological type (same lineage) in a biological sample from the patient. In embodiments where a plurality of white blood cells are interrogated, the methods are useful in allowing a practitioner to distinguish between populations of PNH Type I, Type II, and Type III white blood cells of the same histological type (same lineage) in order to accurately determine the size of the total abnormal PNH population (i.e., Type II plus Type III cells) as compared to the total number of white blood cells of the same histological type in the plurality (and/or allow the practitioner to determine the percentage of PNH Type II white blood cells in the plurality). First, a population of cells (e.g., white blood cells, red blood cells, or a combination of white and red blood cells) is contacted with a reagent that binds to: (i) a GPI moiety or (ii) a GPI-linked protein for a period of time and under conditions that allow for the binding of the reagent to the GPI moiety or GPI-linked protein if present on the surface of cells present in the sample. The population of cells can be present in a biological sample (e.g., a whole blood sample; see the section entitled "Biological Samples and Sample Collection"), e.g., a biological sample obtained from a patient. For example, cells present in a whole blood sample from a patient can be contacted with an aerolysin protein (e.g., a non-lytic form of aerolysin) or an antibody that binds to a GPI moiety or a GPI-anchored protein such as CD59. See, e.g., Hall and Rosse (1996) *Blood* 87(12):5332-5340 and U.S. Pat. No. 6,593,095. At least a portion of the cells (e.g., white blood cells or RBCs) contacted with the reagent can be distinguished based on the amount of reagent bound to the surface of the cells. For example, where a detectably-labeled reagent was used, the amount of reagent bound to the surface can be determined as a function of the total amount of signal produced from detectably labeled reagent bound to the surface of the cell. As described above, the amount of binding of the reagent to the cell reflects the amount of expression of GPI moieties and/or GPI-anchored proteins, which are indicative of whether cells are PNH Type III cells (little or no expression of GPI and GPI-anchored proteins), normal cells (Type I cells; having a relatively high level of expression of GPI and GPI-anchored proteins as compared to the Type III cells), and PNH Type II cells (having an intermediate level of expression of GPI and GPI-anchored proteins as compared to Type I cells and Type III cells). The distinguishing or interrogating process can involve, e.g., flow cytometry.

In some embodiments, the methods are used to detect the amount of binding of a reagent to RBCs from a patient sample. In some embodiments, the methods can be used to detect the amount of binding of a reagent to white blood cells from a patient sample. White blood cells that are particularly amenable to evaluation in the diagnostic methods described herein include, e.g., granulocytes and monocytes (e.g., macrophages).

The samples can be from patients who have, are suspected of having, or at risk for developing paroxysmal nocturnal hemoglobinuria (PNH). In some embodiments, the patients have one or more symptoms including, e.g., Coombs negative intravascular hemolysis, elevated LDH levels, recurrent iron deficiency anemia, thrombosis in unusual sites, episodic dysphagia, or abdominal pain.

In some embodiments, to aid in the identification of normal cells or PNH cells, a set of control cell populations can also be subjected to the detection method. The control populations can be evaluated before, concurrently, or after the evaluation of the cell population of interest. As discussed in more detail below, a practitioner can choose to subject a control population of cells known to be PNH Type II cells, a control population of cells known to be PNH Type III cells, and/or a control population of cells known to be normal or Type I cells to the methods to determine the typical amount, or average amount, of binding of the reagent used to a particular type of cell. This control information can be used to classify or identify cells (e.g., white blood cells or red blood cells) of interest as normal cells, PNH Type II cells, and/or PNH Type III cells.

Depending on the particular composition of the cell population within the biological sample, at least some cells of the population can be distinguished from other cells based on a high amount of bound reagent, a low amount of bound reagent, or an intermediate level of bound reagent. In some cases, only cells with a high amount of bound reagent will be present (for example, cells from a healthy patient or a patient who does not have PNH). In some cases, a larger percentage of cells will have little, or no, reagent bound to their surface (for example, white blood cells or RBCs from a PNH patient having a high percentage of PNH Type III cells). In some embodiments, a population of cells contacted with the reagent can be classified into high, low, and intermediate categories based on the amount of reagent bound to the cells.

In some embodiments, one or more cells (e.g., one or more distinguished or interrogated cells) can be classified based on the amount of reagent bound to their cell surface. As exemplified in the working examples and depicted in FIG. 1, individual cells in a population can be readily classified as highly reagent bound, low or poorly reagent bound, and intermediately reagent bound using flow cytometry methods. For example, white blood cells obtained from a patient with PNH are contacted with two different reagents: a first reagent that binds to a GPI moiety (e.g., a detectably-labeled, non-lytic aerolysin protein) and a second reagent that binds to a GPI-anchored protein (e.g., a detectably-labeled antibody that binds to human CD24). The first reagent and second reagent are labeled with different detectable labels. The contacted cells are then subjected to flow cytometry. An artisan skilled in the art of flow cytometry would be readily able to use the methods to distinguish between cells based on the amount of binding of each reagent to the cells. See, e.g., Macey (2007) "Flow Cytometry: principles and applications," Humana Press (ISBN: 1588296911) and Brodsky et al. (2000) *Am J Clin Pathol* 114:459-466. As shown in FIG. 1, the flow cytometry methods can readily be used to classify granulocytes obtained from a PNH patient as having a high amount of binding of each of the reagents (cell population at upper right; normal or Type I cells), a low amount of binding of each reagent (cell population at lower left; Type III cells), and an intermediate amount of binding of each reagent (cell population at bottom center; Type II cells).

The classification of a cell can be performed by comparing the amount of the reagent bound to the cell to a control amount (e.g., a control amount of binding of the reagent to PNH Type I cells, PNH Type II cells, and/or PNH Type III cells). The control amount of binding of the reagent to PNH Type I cells can be based on, e.g., the average amount of observed binding of the reagent to cells of the same histological type obtained from one or more (e.g., two, three, four, five, six, seven, eight, nine, 10, 15, 20, 25, 30, 35, or 40 or more) healthy individuals. The control amount of binding of the reagent to PNH Type III cells can be based on, e.g., the average amount of binding observed to cells of the same type obtained from one or more (e.g., two, three, four, five, six, seven, eight, nine, 10, 15, 20, 25, 30, 35, or 40 or more) patients with PNH. The control amount of binding of the reagent to PNH Type II cells can be based on, e.g., the average amount of binding observed to cells of the same type obtained from one or more (e.g., two, three, four, five, six, seven, eight, nine, 10, 15, 20, 25, 30, 35, or 40 or more) patients with PNH and having a detectable population of PNH Type II cells of the same histological type (same lineage). For example, to classify a white blood cell of interest based on the amount of reagent bound to the surface of the cell, a practitioner can compare the amount of reagent bound to the cell with the typical amount, or average amount, of reagent bound to a white blood cell known to be a PNH Type I white blood, a white blood cell known to be a PNH Type II white blood cell, and/or a white blood cell known to be a PNH Type III white blood cell.

In some embodiments, the distinguishing or classifying of a cell (e.g., a white blood cell or RBC) of interest can be performed by determining whether the amount of a reagent bound to the cell falls within a predetermined range indicative of PNH Type I cells, PNH Type II cells, or PNH Type III cells of the same histological type. In some embodiments, the distinguishing or classifying of a hematopoietic cell of interest can include determining if the amount of reagent bound to the surface of the cell falls above or below a predetermined cut-off value. A cut-off value is typically the amount of reagent bound to the surface of a cell (or the amount of signal detected from a cell) above or below which is considered indicative of a certain class of cells, namely PNH Type I cells, PNH Type II cells, or PNH Type III cells.

Some cut-off values are not absolute in that diagnostic correlations (e.g., an amount of reagent bound to the surface of the cell and likelihood that the cell is a PNH Type II cell) can still remain significant over a range of values on either side of the cutoff. It is understood that refinements in optimal cut-off values could be determined depending on the quality of reagents used, the sophistication of statistical methods and detection device (e.g., flow cytometry) used, and on the number and source of samples interrogated. Therefore, cut-off values can be adjusted up or down, on the basis of periodic re-evaluations or changes in methodology or sample distribution.

As used herein, "thrombocytopenia" refers to a condition in which a patient has a platelet count of less than 200,000 (e.g., less than 150,000; less than 140,000; less than 130,000; less than 120,000; less than 110,000; less than 100,000; or less than 90,000) platelets per µL of blood. In some embodiments, a patient with thrombocytopenia has a platelet count of less than 100,000 platelets per µL of blood.

As described above, information related to the percentage of PNH Type II cells can be used in methods for determining whether a patient is at increased risk for developing thrombosis. The information related to the percentage of PNH Type II cells (e.g., Type II white blood cells and/or Type II red blood cells) in a biological sample from a patient can be communicated (e.g., electronic or printed form) to a medical practitioner to be used by the practitioner for selecting an appropriate therapeutic regimen for the patient. Based on a PNH Type II white blood cell population of at least 1.2 (e.g., at least 1.2, 1.5, 2, 3, 5, 7, 9, 10, 12, 15, 17, 20, 22, 25, 27, 30, 32, 35, 37, 40, 42, 45, 47, 50, 52, 55, 57, 60, 62, 65, or 65.3 or more) %, as compared to the total number of white blood cells of the same histological type in the biological sample tested, the practitioner may determine that the patient is at risk of developing thrombocytopenia, or may likely be thrombocytopenic. Likewise, a patient with a PNH Type II RBC population of at least 0.02 (e.g., at least 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 55, 60, 65, 70, 71, 71.3, or 75 or more) % of the total RBC in the biological sample tested is much more likely to be thrombocytopenic than a patient who does not have a detectable PNH Type II RBC population or a patient with a PNH Type II RBC population lower than 0.02%. A patient with a PNH Type II white blood cell population of at least 1.2% or a PNH Type II red blood cell population of at least 0.02% can be, e.g., at least 1.5 (e.g., 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 20, 30, or even 40 or more) times as likely to develop a thrombus than a normal individual or a patient that does not have that percentage of PNH Type II cells.

The medical practitioner may request additional tests to determine the platelet counts in the patient. Methods for determining platelet counts in a blood-derived sample from a subject are well known in the art of medicine and described in, e.g., Sallah et al. (1998) *Postgraduate Medicine* 103: 209-210; Kottke-Marchant (1994) *Hematol Oncol Clin North Am.* 8:809-853; Redei et al. (1995) *J Crit Illn* 10:133-137; Butkiewicz et al. (2006) *Thrombosis Research* 118(2): 199-204; Tomita et al. (2000) *Am J Hematol* 63(3):131-135; and Schrezenmeier et al. (1998) *Br J Haematol* 100(3):571-576.

If the patient is determined by the medical practitioner to be thrombocytopenic or to likely be thrombocytopenic, the practitioner may select, prescribe, or administer to the patient an anti-thrombocytopenic therapy. The anti-thrombocytopenic therapy can be, e.g., a corticosteroid, platelet transfusion, a splenectomy, or a platelet production-stimulating agent. The platelet production-stimulating agent can be, e.g., thrombopoietin (TPO) or a thrombopoietin mimetic. See, e.g., Kuter and Begley (2002) *Blood* 100:3457-3469; Li et al. (2001) *Blood* 98:3241-3248; and Vadhan-Raj et al. (2000) *Ann Intern Med* 132:364-368. A TPO mimetic peptide can have the amino acid sequence depicted in FIG. 5 of U.S. Patent Application Publication No. 20030049683, the disclosure of which (particularly FIG. 5) is incorporated by reference in its entirety.

If the percentage of PNH Type II white blood cells in a biological sample from a patient is about 1.2%, the medical practitioner may also determine that the patient is at an increased risk for developing thrombosis. The medical practitioner may then select for the patient an appropriate anti-thrombotic therapy. For example, the practitioner may select, prescribe, or administer to the patient an anticoagulant or thrombolytic agent. The anticoagulant can be, e.g., coumadin, heparin, or derivatives thereof. The thrombolytic agent can be, e.g., a tissue plasminogen activator (e.g., Retavase™, Rapilysin™), streptokinase, or a urokinase-type plasminogen activator.

In some embodiments, a patient determined to have a PNH Type II white blood cell population of greater than or equal to 1.2% or a PNH Type II red blood cell population of greater than or equal to 0.02% can be diagnosed as having PNH. In some embodiments, a patient diagnosed with having PNH or a previously diagnosed PNH patient who is determined to have a PNH Type II white blood cell population greater than or equal to 1.2% or a PNH Type II red blood cell population that is greater than or equal to 0.02% can be prescribed and/or treated with a complement inhibitor.

Any compounds which bind to or otherwise block the generation and/or activity of any of the human complement components may be utilized in accordance with the present disclosure. For example, an inhibitor of complement can be, e.g., a small molecule, a nucleic acid or nucleic acid analog, a peptidomimetic, or a macromolecule that is not a nucleic acid or a protein. These agents include, but are not limited to, small organic molecules, RNA aptamers, L-RNA aptamers, Spiegelmers, antisense compounds, double stranded RNA, small interfering RNA, locked nucleic acid inhibitors, and peptide nucleic acid inhibitors. In some embodiments, a complement inhibitor may be a protein or protein fragment.

In some embodiments, antibodies specific to a human complement component are useful herein. Some compounds include antibodies directed against complement components C1, C2, C3, C4, C5 (or a fragment thereof; see below), C6, C7, C8, C9, Factor D, Factor B, Factor P, MBL, MASP-1, and MASP-2, thus preventing the generation of the anaphylatoxic activity associated with C5a and/or preventing the assembly of the membrane attack complex associated with C5b.

Also useful in the present methods are naturally occurring or soluble forms of complement inhibitory compounds such as CR1, LEX-CR1, MCP, DAF, CD59, Factor H, cobra venom factor, FUT-175, complestatin, and K76 COOH. Other compounds which may be utilized to bind to or otherwise block the generation and/or activity of any of the human complement components include, but are not limited to, proteins, protein fragments, peptides, small molecules, RNA aptamers including ARC187 (which is commercially available from Archemix Corporation, Cambridge, Mass.), L-RNA aptamers, spiegelmers, antisense compounds, serine protease inhibitors, molecules which may be utilized in RNA interference (RNAi) such as double stranded RNA including small interfering RNA (siRNA), locked nucleic acid (LNA) inhibitors, peptide nucleic acid (PNA) inhibitors, etc.

In some embodiments, the complement inhibitor inhibits the activation of complement. For example, the complement inhibitor can bind to and inhibit the complement activation activity of C1 (e.g., C1q, C1r, or C1s) or the complement inhibitor can bind to and inhibit (e.g., inhibit cleavage of) C2, C3, or C4. In some embodiments, the inhibitor inhibits formation or assembly of the C3 convertase and/or C5 convertase of the alternative and/or classical pathways of complement. In some embodiments, the complement inhibitor inhibits terminal complement formation, e.g., formation of the C5b-9 membrane attack complex. For example, an antibody complement inhibitor may include an anti-C5 antibody. Such anti-05 antibodies may directly interact with C5 and/or C5b, so as to inhibit the formation of and/or physiologic function of C5b. Exemplary anti-C5 antibodies include, e.g., eculizumab (Soliris®; Alexion Pharmaceuticals, Inc., Cheshire, Conn.; see, e.g., Kaplan (2002) *Curr Opin Investig Drugs* 3(7):1017-23; Hill (2005) *Clin Adv Hematol Oncol* 3(11):849-50; and Rother et al. (2007) *Nature Biotechnology* 25(11):1256-1488) and pexelizumab (Alexion Pharmaceuticals, Inc., Cheshire, Conn.; see, e.g., Whiss (2002) *Curr Opin Investig Drugs* 3(6):870-7; Patel et al. (2005) Drugs Today (Barc) 41(3):165-70; and Thomas et al. (1996) *Mol Immunol.* 33(17-18):1389-401).

Methods for administering an appropriate anti-thrombotic therapy and/or an anti-thrombocytopenic therapy to a patient in need thereof are well known in the art of medicine.

In some embodiments, methods for determining whether a patient is at an increased risk for developing thrombobocytopenia or thrombosis can be aided by computer. For example, the methods can include receiving data including a medical profile of a PNH patient, the profile comprising information on the percentage of PNH Type II white blood cells of the total white blood cells of the same histological type (same lineage) in a biological sample from the patient; and processing at least the portion of the data containing the information to determine whether the patient is at an increased risk for developing thrombosis. In another example, the methods can include providing information on the percentage of PNH Type II white blood cells of the total white blood cells of the same histological type in a biological sample from the patient; inputting the information into a computer; and calculating a parameter indicating whether the patient is at an increased risk for thrombosis using the computer and the input information. The relative risk of the patient for developing thrombocytopenia or thrombosis can be output by the computer in print and/or can be stored on a computer-readable medium.

Kits

Also featured herein are kits for use in: determining whether a biological sample from a patient contains a PNH Type II white blood cell population and/or determining if a patient is at increased risk for developing thrombocytopenia or thrombosis. The kits can include, e.g., one or more of detectably-labeled conjugates selected from: an aerolysin conjugate (e.g., a non-lytic variant aerolysin protein conjugate) or conjugates of antibodies that bind to GPI-anchored proteins. The kits can also include a control sample containing a GPI expressing cell or GPI bound particle; and optionally, instructions for detecting the presence of a GPI expressing cell. The kits can also include one or more means for obtaining a biological sample (e.g., a blood sample) from a human and/or any of the kit components described above.

The following examples are intended to illustrate, not limit, the invention.

EXAMPLES

Example 1. Materials and Methods

A total of 2,921 patient peripheral blood samples were obtained to test for the presence of PNH Type II cells and PNH Type III cells. The blood samples were drawn into sterile vials containing EDTA.

To determine the percentage of normal white blood cells (Type I cells), PNH Type II, and PNH Type III white blood cells present in each of the patient samples, the peripheral blood was mixed and stained with one or more of the following conjugates: a non-lytic aerolysin variant protein conjugated to AlexaFluor® 488 (Protox Biotech FL2-S), an anti-CD24 antibody conjugated to phycoerythrin (PE) (Beckman Coulter Clone ALB9), an anti-CD15 antibody conjugated to PC5 (Clone 80H5), and an anti-CD45 antibody conjugated to PC7 (Clone J.33). After incubation of the blood with one or more of the above reagents for 15-30 minutes at room temperature, the blood was lysed with Immunoprep™ (Beckman Coulter) and washed twice with PBA buffer (phosphate-buffered saline, 1% bovine serum albumin, and 10 mM $NaN_3$). Cells are then re-suspended in PBA buffer and analyzed using the FC 500 Flow Cytometer (Beckman Coulter). If a PNH Type II or Type III granulocyte population was identified, the monocytes were also interrogated for Type II or Type III population using patient blood contacted with one or more of the following conjugates: a non-lytic aerolysin variant protein conjugated to AlexaFluor® 488 (Protox Biotech FL2-S), an antibody that binds to CD33 conjugated to phycoerythrin (PE) (Clone D3HL60.251), an antibody that binds to CD14 conjugated to ECD (Clone RMO52), an antibody that binds to CD64 conjugated to PC5 (Clone 22), and an antibody that binds to CD45 conjugated to PC7 (Clone J.33), which allowed for lineage-specific gating on monocytes.

To determine the percentage of normal red blood cells (Type I cells), PNH Type II, and PNH Type III red blood cells 20 µl of peripheral blood in EDTA was placed in 3 mL of phosphate buffered saline (PBS) and mixed thoroughly. 50 µl of diluted patient blood was contacted with one or more of the following conjugates: an anti-CD235a antibody conjugated to FITC (Beckman Coulter clone 11E4B-7-6/KC16) and an anti-CD59 antibody conjugated to PE (Invitrogen Clone MEM-43). The blood and conjugates were incubated at room temperature in the dark for one hour while vortexing every 15 minutes. After the one hour incubation, the blood was washed twice with PBS, resuspended in PBS, and analyzed on an FC 500 Flow Cytometer (Beckman Coulter).

Example 2

Whole blood samples from 2,921 patients, which samples were submitted for diagnostic testing for PNH, were analyzed using a high-sensitivity flow cytometry-based assay to detect the expression level of GPI and GPI-anchored proteins on white blood cells (particularly granulocytes) to thereby determine the Type I, PNH Type II, and PNH Type III white blood cell (granulocyte) populations in each of the samples. The assay was also used to detect the Type I, PNH Type II, and PNH Type III red blood cell populations in each of the patient samples. The methods employed a fluorescently-labeled non-lytic aerolysin protein variant along with antibodies to specific GPI-anchored lineage-specific protein antigens. An exemplary flow-cytometry analysis of one patient sample is depicted in FIG. 1. Cells from a whole blood sample were contacted with the fluorescently-labeled aerolysin reagent (Alexa Fluor) and a phycoeyrthrin (PE)-labeled antibody that binds to the GPI-anchored protein CD24. The cells of the whole blood sample were subjected to flow cytometry analysis and the granulocytes therein displayed based on the amount of signal detected from each reagent bound to the surface of the granulocytes. As shown in FIG. 1, granulocytes with the highest amount of signal detected from the AlexaFluor and PE labels (upper right; Type I cells) were separated from populations of granulocytes having a very low or absent signal (lower left; Type III granulocytes) and granulocytes producing an intermediate amount of signal (middle population; Type II granulocytes).

The PNH red blood cell populations were interrogated using two reagents: a detectably-labeled antibody that binds to CD235 and a detectably-labeled reagent that binds to CD59. The PNH white blood cell populations were interrogated using the detectably-labeled aerolysin protein and several antibodies to GPI-anchored lineage-specific cell surface proteins including CD24, CD14, CD16, CD66b, and CD55.

216 of the patient samples had a detectable PNH Type III granulocyte population that was >0.01% of the total number of granulocytes in the sample and an absolute count of at least 50 PNH Type III granulocytes. Clinical information related to several parameters (e.g., hemoglobin levels, LDH levels, and platelet counts) was available for 162 of these patients (see Table 1).

TABLE 1

Clinical Features of Patients with a Detectable PNH Type III or II granulocyte population (where clinical data were available.)

| | Cases with Type II granulocytes (N = 19) | Cases without Type II granulocytes (N = 143) | P-value Wilcoxin |
|---|---|---|---|
| Median (range) Total PNH granulocyte population (%) | 87.20 (9.2-99.5) | 11.40 (0.01-99.9) | <0.01 |
| Median (range) PNH Type II granulocyte population (%) | 7.10 (1.2-65.3) | n/a | n/a |
| Median (range) PNH Type III granulocyte population (%) | 76.0 (4.5-96.4) | 11.40 (0.01-99.9) | 0.02 |
| Median (range) PNH Type II RBC population (%) | 3.30 (0.02-71.3) | 0.20 (0-76.20) | <0.01 |
| Median (range) PNH Type III RBC population (%) | 16.10 (0.03-86.70) | 2.90 (0-92.9) | 0.01 |
| Median white blood cell ($\times 10^9$/L) | 3.80 | 4.20 | 0.44 |
| Median absolute neutrophil count (cells/µL) | 2.07 | 2.15 | 0.70 |
| Median RBC ($\times 10^{12}$/L) | 3.08 | 3.14 | 0.80 |
| Median hemoglobin (g/dL) | 10.6 | 10.4 | 0.87 |
| Median LDH (IU/L) | 336 | 315 | 0.88 |
| Median platelets ($\times 10^9$/L) | 54 | 116 | 0.01 |
| Platelets < 100 × $10^9$/L (%) | 68.4 (13/19) | 44.0 (62/141) | 0.05* |

*Fisher's exact test.

Of the samples from patients in which clinical information was available, 19 (8.8%) patient samples contained distinct Type II granulocyte populations, ranging from 1.2-65.3% of the total granulocyte population, with a median clone size of approximately 7%. In 4 of the 19 patient samples, the Type II granulocyte population represented >50% of the total abnormal population (e.g., PNH Type II and Type III cells). In 10 of the 19 patient samples, a PNH Type II monocyte population was also detected. An evaluation of the ability of various antibodies, specific for individual GPI-linked proteins found on granulocytes, to detect PNH Type II granulocytes indicated that the Type II granulocyte population was detectable in all cases using the detectably-labeled aerolysin reagent, but in decreasing percentages using antibodies specific for CD66b (88%), CD55 (50%), CD24 (47%), and CD16 (0%) (see Table 2). These results indicate that the aerolysin-based conjugate is particularly useful to accurately detect PNH Type II granulocyte populations in patient samples.

TABLE 2

Detection of Type II granulocytes using aerolysin or other anti-GPI anchored-protein antibodies.

| Aerolysin | CD24 | CD66b | CD55 | CD16 |
|---|---|---|---|---|
| 19/19 (100%) | 9/19 (47%) | 8/9 (88%) | 4/8 (50%) | 0/9 (0%) |

Patient samples containing PNH Type II granulocyte populations had a significantly larger median total combined PNH Type II and PNH Type III granulocyte population than those without Type II granulocytes (87% versus 11%; p=0.0003), as well as larger median Type II and Type III RBC populations, which reflects an increased ability of the method to detect PNH Type II white blood cell populations in patient samples with overall larger PNH cell populations.

Figure 2:
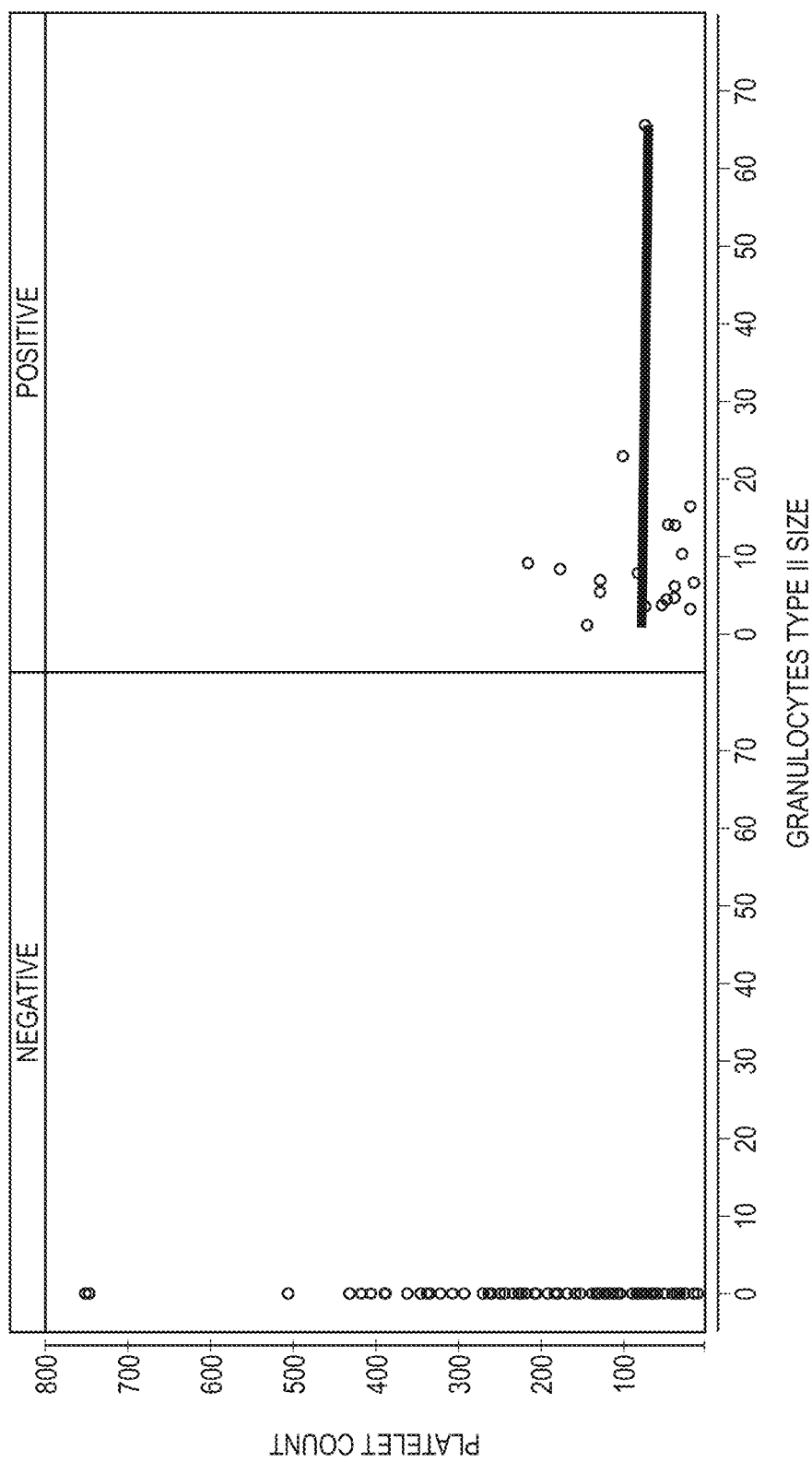
FIG. 2 is a scatter plot depicting the absolute platelet count versus the percentage of PNH Type II granulocytes in the blood of patients with PNH. The Y-axis represents the platelet count in 1 μL of patient blood ($\times 10^{-3}$) and the X-axis represents the percentage of PNH Type II granulocytes within the total granulocyte population. The left half of the plot is a distribution of the platelet counts observed among PNH patients (N=141) that have no detectable PNH Type II granulocyte populations. The right half of the plot is a distribution of the platelet counts observed among PNH patients (N=19) who have detectable PNH Type II granulocyte populations.

After comparison with the clinical data it was discovered that patient samples with PNH Type II granulocyte populations also had lower median platelet (plt) counts ($54 \times 10^9$/L; p<0.01). See FIG. 2. Patient samples with PNH Type II granulocyte populations had similar peripheral white blood cell counts, peripheral red blood cell counts, absolute neutrophil counts, and hemoglobin (Hgb) levels, compared to patient samples without detectable Type II granulocyte populations (Table 1), indicating that differences in platelet counts are likely not due to differences in underlying bone marrow production. In other words, while the disclosure is in no way limited by any particular theory or mechanism of action, as PNH patients have dysregulated complement control due to the lack of the GPI-linked complement regulatory proteins CD55 and CD59, the decreased platelet counts observed in patients with detectable PNH Type II granulocyte clones may be due to increased terminal complement-mediated platelet consumption or destruction, which may in turn be associated with thrombosis, the leading cause of death among PNH patients.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A method for treating a patient, the method comprising administering to a patient in need thereof one or both of an anti-thrombotic therapy and an anti-thrombocytopenic therapy, wherein the patient has been determined to have a paroxysmal nocturnal hemoglobinuria (PNH) Type II white blood cell population that is between 1.2% and 65.3%, inclusive of 1.2% and 65.3%, of the patient's total granulocytes.

2. The method of claim 1, wherein the anti-thrombotic therapy is an anticoagulant.

3. The method claim 1, wherein the anti-thrombocytopenic therapy is a platelet transfusion.

4. The method of claim 1, wherein a non-lytic variant form of aerolysin protein is used to determine the percentage of PNH Type II white blood cells.

5. The method of claim 2, wherein the anticoagulant is coumadin, heparin, or derivatives thereof.

6. The method claim 1, wherein the anti-thrombocytopenic therapy is a corticosteroid.

7. The method of claim 1, wherein the anti-thrombocytopenic therapy is a splenectomy.

8. The method of claim 1, wherein the anti-thrombocytopenic therapy is a platelet production-stimulating agent.

9. The method of claim 8, wherein the platelet production-stimulating agent is thrombopoietin (TPO) or a thrombopoietin mimetic.

10. The method of claim 2, wherein the anticoagulant is coumadin.

11. The method of claim 2, wherein the anticoagulant is heparin.

12. The method of claim 1, wherein the anti-thrombotic therapy is a thrombolytic agent.

13. The method of claim 12, wherein the thrombolytic agent is a tissue plasminogen activator.

14. The method of claim 12, wherein the thrombolytic agent is streptokinase.

15. The method of claim 12, wherein the thrombolytic agent is a urokinase-type plasminogen activator.

16. The method of claim 1, comprising administering to the patient a complement inhibitor.

17. The method of claim 16, comprising administering to the patient an anti-C5 antibody.

18. The method of claim 17, comprising administering to the patient eculizumab.

19. A method for treating a patient, the method comprising administering to a patient in need thereof eculizumab and one or both of an anti-thrombotic therapy and an anti-thrombocytopenic therapy, wherein the patient has been determined to have a paroxysmal nocturnal hemoglobinuria (PNH) Type II white blood cell population that is between 1.2% and 65.3%, inclusive of 1.2% and 65.3%, of the patient's total granulocytes.

* * * * *